(12) United States Patent
Walters et al.

(10) Patent No.: US 11,518,751 B2
(45) Date of Patent: Dec. 6, 2022

(54) PHOTOCHROMIC INDENO-FUSED NAPHTHOPYRAN COMPOUNDS WITH REDUCED TEMPERATURE DEPENDENCE

(71) Applicant: Transitions Optical, Ltd., Tuam (IE)

(72) Inventors: Robert W. Walters, Murrysville, PA (US); Chien-Yang Chiu, Export, PA (US); Anu Chopra, Pittsburgh, PA (US); Darrin R. Dabideen, Pittsburgh, PA (US); Sujit Mondal, Gibsonia, PA (US); Nick J. Parise, Pittsburgh, PA (US); Wenjing Xiao, Murrysville, PA (US)

(73) Assignee: Transitions Optical, Ltd., Tuam (IE)

( * ) Notice: Subject to any disclaimer, the term of this patent is extended or adjusted under 35 U.S.C. 154(b) by 66 days.

(21) Appl. No.: 17/058,888

(22) PCT Filed: May 28, 2018

(86) PCT No.: PCT/EP2018/063893
§ 371 (c)(1),
(2) Date: Nov. 25, 2020

(87) PCT Pub. No.: WO2019/228604
PCT Pub. Date: Dec. 5, 2019

(65) Prior Publication Data
US 2021/0198226 A1 Jul. 1, 2021

(51) Int. Cl.
*C07D 311/94* (2006.01)
*C07D 413/10* (2006.01)
(Continued)

(52) U.S. Cl.
CPC .......... *C07D 311/94* (2013.01); *C07D 413/10* (2013.01); *G02B 1/04* (2013.01); *G02B 5/23* (2013.01); *G03C 1/73* (2013.01)

(58) Field of Classification Search
CPC ...... C07D 311/94; C07D 413/10; G02B 1/04; G02B 5/23; G03C 1/73
See application file for complete search history.

(56) References Cited

U.S. PATENT DOCUMENTS 5,645,767 A * 7/1997 Van Gemert ........ C08K 5/1545
546/281.1
6,113,814 A 9/2000 Gemert et al.
(Continued)

FOREIGN PATENT DOCUMENTS

EP 2457915 A1 7/2010
EP 2463280 A1 8/2010
(Continued)

OTHER PUBLICATIONS

Ikawa et al., "Pd-Catalyzed Amidations of Aryl Chlorides Using Monodentate Biaryl Phosphine Ligands: A Kinetic, Computational, and Synthetic Investigation", J. Am. Chem. Soc., 2007, pp. 2-45, Cambridge.
(Continued)

*Primary Examiner* — Bijan Ahvazi
(74) *Attorney, Agent, or Firm* — The Webb Law Firm

(57) ABSTRACT

A photochromic compound including a core skeletal structure represented by the following Formula (I),
(Continued)

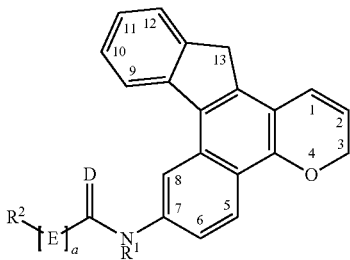

Formula (I)

wherein D is oxygen or sulfur; E is oxygen, sulfur, or $NR^{2'}$; a is 0 or 1; $R^1$ is hydrogen, or substituted or unsubstituted alkyl; $R^2$ and $R^{2'}$ are each independently selected from hydrogen, substituted or unsubstituted alkyl, substituted or unsubstituted aryl, substituted or unsubstituted heteroaryl, or substituted or unsubstituted heterocycloalkyl; and the photochromic compound is a thermally reversible photochromic compound.

15 Claims, 2 Drawing Sheets

(51) Int. Cl.
G02B 1/04 (2006.01)
G02B 5/23 (2006.01)
G03C 1/73 (2006.01)

(56) References Cited

U.S. PATENT DOCUMENTS

| | | | | |
|---|---|---|---|---|
| 6,146,554 | A * | 11/2000 | Melzig | C07D 311/94 546/281.1 |
| 6,555,028 | B2 * | 4/2003 | Walters | G02B 5/23 546/281.1 |
| 7,320,826 | B2 | 1/2008 | Kumar et al. | |
| 7,521,004 | B2 | 4/2009 | Momoda et al. | |
| 8,308,996 | B2 * | 11/2012 | Takahashi | C07D 311/96 544/31 |
| 8,518,546 | B2 | 8/2013 | He et al. | |
| 8,859,097 | B2 * | 10/2014 | Chopra | C07D 311/94 524/110 |
| 9,028,728 | B2 * | 5/2015 | Bancroft | C09K 9/02 544/31 |
| 9,334,439 | B2 | 5/2016 | DeMeio et al. | |
| 10,371,866 | B2 | 8/2019 | Frease et al. | |
| 10,954,397 | B2 | 3/2021 | Haley et al. | |
| 2004/0014995 | A1 * | 1/2004 | Kawabata | G03C 1/685 568/325 |
| 2012/0156521 | A1 * | 6/2012 | He | C07D 311/92 428/688 |
| 2012/0270071 | A1 * | 10/2012 | Takahashi | C07D 241/38 544/70 |

FOREIGN PATENT DOCUMENTS

| | | |
|---|---|---|
| JP | H10508031 A | 8/1998 |
| JP | 2002524558 A | 8/2002 |
| JP | 2016519691 A2 | 7/2016 |
| WO | 9915518 A1 | 4/1999 |
| WO | 2012082236 A1 | 6/2012 |
| WO | 2013086248 A1 | 6/2013 |
| WO | 2016142496 A1 | 9/2016 |
| WO | 2017030545 A1 | 2/2017 |

OTHER PUBLICATIONS

Tundo et al., "Dimethyl Carbonate as an Ambident Electrophile", J. Org. Chem., 2005, pp. 2219-2224, vol. 70:6, Italy.

* cited by examiner

PHOTOCHROMIC INDENO-FUSED NAPHTHOPYRAN COMPOUNDS WITH REDUCED TEMPERATURE DEPENDENCE

CROSS-REFERENCE TO RELATED APPLICATION

This application is the United States national phase of International Application No. PC/EP2018/06.389.3 filed May 28, 2018, the disclosure of which is hereby incorporated by reference in its entirety.

FIELD

The present invention relates to fused ring photochromic compounds, such as photochromic indeno-fused naphthopyran compounds, and photochromic compositions and photochromic articles that include such photochromic compounds.

BACKGROUND

Photochromic compounds undergo a transformation from one state (or form) to another state in response to certain wavelengths of electromagnetic radiation (i.e., "actinic radiation"). Each state has a characteristic absorption spectrum. For example, many photochromic compounds transform from an unactivated (e.g., bleached or substantially colorless) state to an activated (e.g., tinted) state upon exposure to actinic radiation. When the actinic radiation is removed, the photochromic compounds reversibly transform from the activated state back to the unactivated state. A "thermally reversible photochromic compound" is a photochromic compound that converts from an unactivated state to an activated state in response to actinic radiation, and reverts back to the unactivated state in response to thermal energy. The activation reaction (from unactivated to activated) is primarily photochemical while the deactivation reaction (from activated to deactivated) is primarily thermal. Such photochromic compounds display what is called "temperature dependence" or a "temperature dependence effect".

The "temperature dependence effect" is a result of a shift in the equilibrium concentrations between the unactivated state and the activated state due to temperature. As the temperature increases, the equilibrium is shifted towards the unactivated (e.g., bleached) state. As the temperature decreases, the equilibrium is shifted towards the activated (e.g., tinted) state. Articles and materials containing these photochromic compounds therefore will present a different response depending on their temperature. Because the forward reaction is light activated and the reverse reaction is thermally driven, thermally reversible photochromic compounds, when activated, tend to be darker at colder temperatures and clearer at warmer temperatures.

The temperature dependence effect is a particular problem with photochromic articles, such as photochromic eyewear lenses. The coloration of the photochromic article is affected by the temperature at which it is used. For example, a photochromic article incorporating a thermally reversible photochromic compound may not get sufficiently dark when the ambient temperature is hot and/or may get too dark when the ambient temperature is cold. By "ambient temperature" is meant the temperature of the environment in immediate contact with the photochromic article. For example, for photochromic eyewear lenses worn by a wearer, the ambient temperature would be the temperature of the air in immediate contact with the photochromic eyewear lenses.

Photochromic compounds can be characterized with regard to various properties, such as but not limited to: fade rate; change in optical density ($\Delta OD$); the change in optical density ($\Delta OD$) at saturation; sensitivity ($\Delta OD/Min$); the efficiency at which the photochromic compound absorbs radiation required to activate the photochromic compound (chromaticity); and dichroic properties (such as in the case of photochromic-dichroic compounds), which can be quantified with regard to absorption ratio (AR) values. The change in optical density measures the change from the unactivated state to the activated state.

One way to quantify the temperature dependence of photochromic compounds is by measuring the difference in the optical density of the activated state at two temperatures. When comparing photochromic compounds, all else being equal, the compound with the smaller difference in optical density between two temperatures in the activated state is considered to have a smaller temperature dependence, i.e., a reduced temperature dependence effect. It would be desirable to provide a photochromic compound having a reduced temperature dependence compared to known photochromic compounds. For example, it would be desirable to provide new photochromic indeno-fused naphthopyran compounds with reduced temperature dependence.

SUMMARY

A photochromic compound comprises a core skeletal structure represented by the following Formula (I),

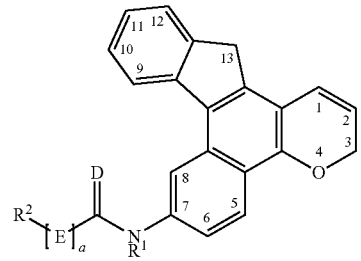

Formula (I)

wherein D is oxygen or sulfur; E is oxygen, sulfur, or $NR^{2'}$; a is 0 or 1; $R^1$ is hydrogen, or substituted or unsubstituted alkyl; $R^2$ and $R^{2'}$ are each independently selected from hydrogen, substituted or unsubstituted alkyl, substituted or unsubstituted aryl, substituted or unsubstituted heteroaryl, or substituted or unsubstituted heterocycloalkyl; and the photochromic compound is a thermally reversible photochromic compound.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

DETAILED DESCRIPTION

Figure 1:
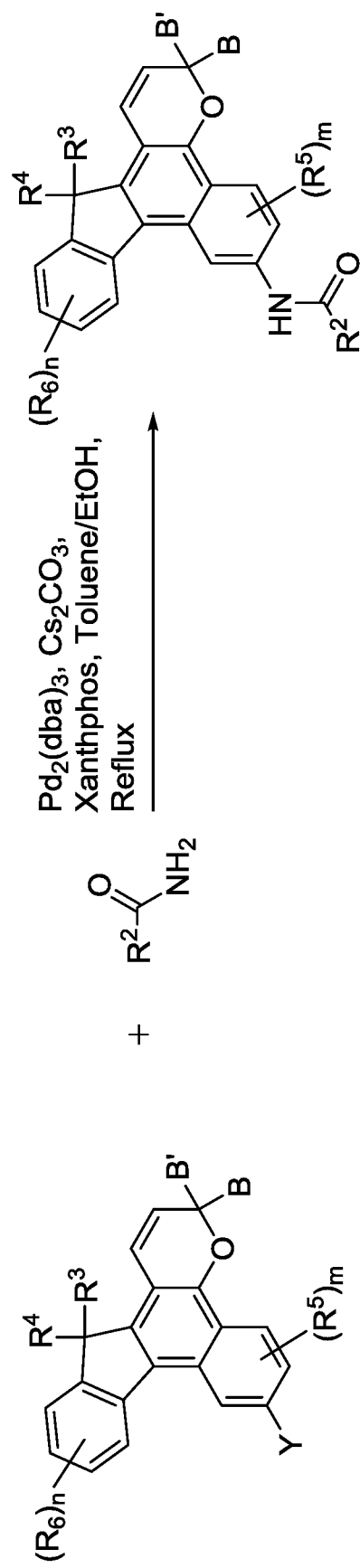
FIG. 1 illustrates a general scheme, Scheme 1, of an exemplary method for preparing photochromic compounds of the invention.

As used herein, the articles "a", "an", and "the" include plural referents unless otherwise expressly and unequivocally limited to one referent.

As used herein, the term "includes" is synonymous with "comprises."

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

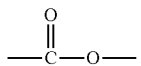

or equivalently —C(O)O—, is inclusive of the right-to-left representation thereof,

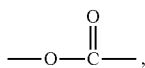

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about." By "about" is meant plus or minus twenty-five percent of the stated value, such as plus or minus ten percent of the stated value. However, this should not be considered as limiting to any analysis of the values under the doctrine of equivalents.

As used herein, molecular weight values of polymers, such as weight average molecular weights (Mw) and number average molecular weights (Mn), are determined by gel permeation chromatography using appropriate standards, such as polystyrene standards.

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means derivatives of acrylic acid and methacrylic acid, inclusive of acrylate esters, methacrylate esters, acrylamides, methacrylamides, acrylic acid and methacrylic acid. As used herein, the term "(meth)acrylic acid" means methacrylic acid and/or acrylic acid.

The photochromic compounds of the present invention are, with some embodiments, also referred to herein as photochromic-dichroic compounds (such as, when they include one or more lengthening groups, such as $L^1$).

The photochromic compounds of the present invention, as described herein, including, but not limited to, photochromic compounds represented by Formula (I), Formula (Ia), Formula (Ib), and Formula (Ic), in each case can optionally further include one or more coproducts, resulting from the synthesis of such compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "dichroic" means capable of absorbing one of two orthogonal plane polarized components of at least transmitted radiation more strongly than the other.

As used herein, the term "photochromic-dichroic" and similar terms, such as "photochromic-dichroic compound", means possessing and/or providing both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

As used herein, and unless stated otherwise or otherwise limited, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein, to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein, the term "optical" means pertaining to or associated with light and/or vision. For example, according to various non-limiting embodiments disclosed herein, the optical article or element or device can be chosen from ophthalmic articles, elements and devices; display articles, elements and devices; windows; mirrors; or active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein, the term "display" means the visible or machine-readable representation of information in words, numbers, symbols, designs or drawings. Non-limiting examples of display elements include screens, monitors, and security elements, such as security marks.

As used herein, the term "window" means an aperture adapted to permit the transmission of radiation therethrough. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over", "deposited over", "provided over", "applied over", "residing over", or "positioned over" mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, recitations relating to ring positions such as, but not limited to, position-x (e.g., position-3 or position-13) means a particular position in the ring structure, such as the core skeletal structure, of a chemical compound, such as the indeno-fused ring photochromic compounds of the present invention, and which are depicted herein in accordance with some embodiments by numbers within the ring structures of representative chemical formulas such as, but not limited to Formulas (I), (Ia), (Ib), and/or (Ic).

By "core skeletal structure" is meant a compound comprising at least the skeletal structure depicted in the associated Formula. The core skeletal structure is provided for purposes of identifying numbered ring positions. However, it is to be understood that, unless specifically shown to the contrary, the core skeletal structure(s) can have one or more atoms or one or more groups (not specifically illustrated on the corresponding Formula) bonded to one or more of the numbered ring positions on the core skeletal structure, which can be the same or different from one another.

The photochromic compounds of the present invention are referred to herein with reference to the term "core skeletal structure," which can be represented by one or more formulas, such as but not limited to Formulas (I), (Ia), (Ib), and/or (Ic).

All documents or portions of documents, such as but not limited to issued patents and patent applications, referred to herein, and unless otherwise indicated, are to be considered to be "incorporated by reference" in their entirety.

As used herein, recitations of "substituted" group, means a group including, but not limited to, alkyl group, heterocycloalkyl group, aryl group, and/or heteroaryl group, in which at least one hydrogen thereof has been replaced or substituted with a group that is other than hydrogen, such as, but not limited to, alkoxy groups; halo groups (e.g., F, Cl, I, and Br); hydroxyl groups; thiol groups; alkylthio groups; ketone groups; aldehyde groups; ester groups; carboxylic acid groups; phosphoric acid groups; phosphoric acid ester groups; sulfonic acid groups; sulfonic acid ester groups; nitro groups; cyano groups; alkyl groups (including aralkyl groups); alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); heteroaryl groups (including poly-fused-ring heteroaryl groups); amine groups, such as —N($R_{11}$')($R_{12}$') where $R_{11}$' and $R_{12}$' are each independently selected, for example, from hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; polyester groups; polyether groups; polycarbonate groups; polyurethane groups; acrylate groups; methacrylate groups; nitrogen-containing heterocycles; or combinations thereof, including those classes and examples as described further herein.

"Aryl group" refers to an aromatic cyclic monovalent hydrocarbon radical, and the term "aromatic" refers to a cyclically conjugated hydrocarbon with a stability (due to delocalization) that is significantly greater than that of a hypothetical localized structure. Examples of aryl groups include $C_6$-$C_{14}$ aryl groups, such as, but not limited to, phenyl, naphthyl, phenanthryl, and anthracenyl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F, Cl or Br.

As used herein, recitations of "linear or branched" groups, such as linear or branched alkyl, are herein understood to include: a methylene group or a methyl group; groups that are linear (or "straight chain"), such as linear $C_1$-$C_{25}$ alkyl groups; and groups that are appropriately branched, such as branched $C_3$-$C_{25}$ alkyl groups.

The term "alkyl" as used herein, means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein, means groups that are appropriately cyclic, such as, but not limited to, $C_3$-$C_{12}$ cycloalkyl (including, but not limited to, cyclic $C_5$-$C_7$ alkyl, or cyclic $C_3$-$C_{10}$ alkyl) groups. Examples of cycloalkyl groups include, but are not limited to, those recited further herein. The term "cycloalkyl" as used herein, also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, means groups that are appropriately cyclic, such as, but not limited to, $C_2$-$C_{12}$ heterocycloalkyl groups, such as $C_5$-$C_7$ heterocycloalkyl groups, such as $C_2$-$C_{10}$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein, also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The term heteroaryl, as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, isoquinoline, and pyrimidinyl.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl," as used herein, includes but is not limited to $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl substituents. Representative heterocycloalkyl groups include, but are not limited to, imidazolyl, tetrahydrofuranyl, tetrahydropyranyl and piperidinyl. Representative aryl groups include, but are not limited to, phenyl, naphthyl, anthracynyl, phenanthrenyl, and tetracenyl (including structural isomers thereof). Representative heteroaryl groups include, but are not limited to, furanyl, pyranyl, pyridinyl, isoquinolinyl, and pyrimidinyl. Representative aralkyl groups include, but are not limited to, benzyl and phenethyl.

The term "nitrogen-containing heterocycle," as used herein, includes, but is not limited to, a nitrogen-containing ring wherein the nitrogen-containing ring is bonded through a ring nitrogen. Examples of nitrogen-containing heterocycles include, but are not limited to, cyclic aminos, such as morpholino, piperidino, and pyrrolidino; and heteroaromatics, such as imidazole, pyrrole, indole, and carbazole.

As used herein, "at least one of" is synonymous with "one or more of", whether the elements are listed conjuctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" or "chosen from" are synonymous with "at least one of", whether the elements are listed conjunctively or disjunctively. For example, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the invention may describe certain features as being "particularly" or "preferably" within certain limitations (e.g., "preferably", "more preferably", or "even more preferably", within certain limitations). It is to be understood that the invention is not limited to these particular or preferred limitations but encompasses the entire scope of the disclosure.

The invention comprises, consists of, or consists essentially of, the following aspects of the invention, in any combination.

The photochromic compounds according to the present invention can be represented by one or more of the core skeletal structures described below. Each available numbered ring position (e.g., 1, 2, 3, 5, 6, 8, 9, 10, 11, 12, and/or 13) of the core skeletal structure of Formula (I) can have covalently bonded thereto hydrogen or a group other than hydrogen, for example, such as a group described herein. Examples of such groups are described below.

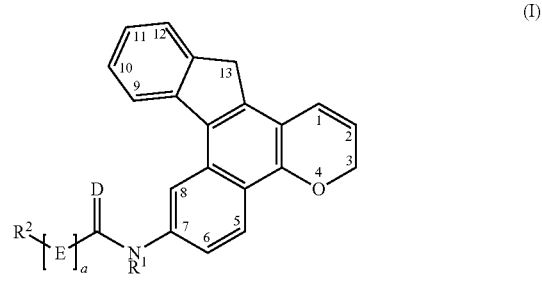

(I)

With reference to Formula (I), D is oxygen or sulfur; E is oxygen, sulfur, or $NR^{2'}$; a is 0 or 1; $R^1$ is hydrogen, or substituted or unsubstituted alkyl; and $R^2$ and $R^{2'}$ are each independently selected from hydrogen, substituted or unsubstituted alkyl, substituted or unsubstituted aryl, substituted or unsubstituted heteroaryl, or substituted or unsubstituted heterocycloalkyl, provided that when $R^2$ is a substituted aryl or substituted heteroaryl, the substituent does not comprise an aromatic group or a cyclic group, and provided that when E is oxygen or sulfur, $R^2$ is not hydrogen. Examples of alkyl groups from which $R^1$ can be selected include, but are not limited to, substituted or unsubstituted $C_1$-$C_{12}$ alkyl. For example, $R^1$ can be selected from hydrogen or methyl. Examples of alkyl groups from which $R^2$ and $R^{2'}$ can be selected from include, but are not limited to, substituted or unsubstituted alkyl. For example, $R^2$ and $R^{2'}$ can be selected from methyl, phenyl, alkoxyphenyl, e.g., 4-methoxyphenyl and 2-methoxyphenyl; haloalkyl phenyl, e.g., perhaloalkyl substituted phenyl and 4-trifluoromethyl phenyl; amino phenyl, e.g., 4-dimethylamino phenyl; alkyl phenyl, e.g., 2-methyl phenyl; or hydroxyphenyl, e.g., 2-hydroxyphenyl.

Each alkyl substituent, each heterocycloalkyl substituent, each aryl substituent, and each heteroaryl substituent herein can in each case be independently selected from one or more of halogen, cyano, nitro, alkyl, alkenyl, alkynyl, haloalkyl, perhaloalkyl, heterocycloalkyl, aryl, heteroaryl, alkoxy, hydroxyl, alkylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a methacrylate group, aryl amino, e.g., diphenyl amino; alkyl amino, e.g., dimethyl amino; cyclic amino, e.g., morpholino, piperidino, or pyrrolidino; heteroaromatics, e.g., imidazole, pyrrole, indole, or carbazole; or combinations thereof; or any other group as long as it does not adversely impact upon the performance properties of the compound, e.g., the photochromic performance properties of the compound. Each amino substituent can be a primary, secondary, or tertiary amine.

Additionally or alternatively, the photochromic compounds of the present invention can be represented by the core skeletal structure of Formula (Ia):

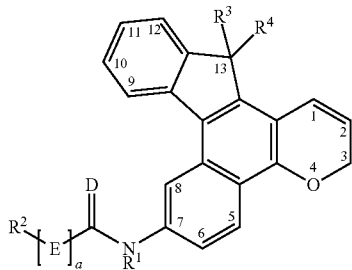

(Ia)

With reference to Formula (Ia), D, E, a, $R^1$, $R^2$, and $R^{2'}$ are as previously described with respect to Formula (I).

As described above, the remaining numbered ring positions (e.g., 1, 2, 3, 5, 6, 8, 9, 10, 11, and/or 12) of the core skeletal structure of Formula (Ia) without a specifically shown substituent can have covalently bonded thereto hydrogen or a group other than hydrogen, for example, such as a group described herein.

With further reference to Formula (Ia), $R^3$ and $R^4$ are each independently selected from hydrogen, substituted or unsubstituted alkyl, substituted or unsubstituted heterocycloalkyl, allyl, substituted or unsubstituted aryl, or substituted or unsubstituted heteroaryl; alkoxy, hydroxyl, alkylthio, ketone, aldehyde, ester, carboxylic acid, carboxylate, siloxane, alkoxysilane, or polysiloxane; a group comprising polyester, polyether, polycarbonate, polyurethane or combinations thereof; or $R^3$ and $R^4$ together form an aliphatic ring having 3 to 20 ring member carbon atoms, a condensed polycyclic ring having an aromatic ring or aromatic hetero ring condensed to the above aliphatic ring, a hetero ring having 3 to 20 ring member atoms, or a condensed polycyclic ring having an aromatic ring or aromatic hetero ring condensed to the above hetero ring, together with the 13-position carbon atom bonded thereto. For example, $R^3$ and $R^4$ together may form a spiro substituent selected from a substituted or unsubstituted spiro-carbocyclic ring, a substituted or unsubstituted spiro-heterocyclic ring, the spiro-carbocyclic ring and spiro-heterocyclic ring being annellated with 0, 1 or 2 aryl rings, each spiro-ring substituent independently being alkyl. For example, $R^3$ and $R^4$ can be each independently selected from substituted or unsubstituted alkyl or substituted or unsubstituted heterocycloalkyl. For example, $R^3$ and $R^4$ can be selected from dimethyl or di-n-propyl.

With further reference to Formula (Ia), each alkyl substituent, each heterocycloalkyl substituent, each aryl substituent, and each heteroaryl substituent can be in each case independently selected from one or more of the substituents described above.

Additionally or alternatively, the photochromic compounds of the present invention can be represented by the core skeletal structure of Formula (Ib):

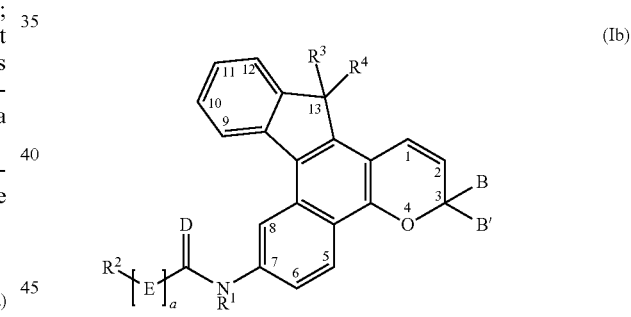

(Ib)

With reference to Formula (Ib), D, E, a, $R^1$, $R^2$, $R^{2'}$, $R^3$, and $R^4$ are as previously described with respect to Formulas (I) and/or (Ia).

As described above, the remaining numbered ring positions (e.g., 1, 2, 5, 6, 8, 9, 10, 11, and/or 12) of the core skeletal structure of Formula (Ib) without a specifically shown substituent can have covalently bonded thereto hydrogen or a group other than hydrogen, for example, such as a group described herein.

With further reference to Formula (Ib), B and B' are each independently selected from substituted or unsubstituted aryl, substituted or unsubstituted heteroaryl, substituted or unsubstituted alkenyl, or substituted or unsubstituted alkynyl, or B and B' together form an aliphatic ring having 3 to 20 ring member carbon atoms, a condensed polycyclic ring having an aromatic ring or aromatic hetero ring condensed to the above aliphatic ring, a hetero ring having 3 to 20 ring member atoms, or a condensed polycyclic ring having an aromatic ring or aromatic hetero ring condensed to the above hetero ring, together with the 3-position carbon atom bonded thereto. For example, B and B' together may form a spiro substituent selected from a substituted or unsubstituted spiro-carbocyclic ring, a substituted or unsubstituted spiro-heterocyclic ring, the spiro-carbocyclic ring and spiro-heterocyclic ring being annellated with 0, 1 or 2 aryl rings, each spiro-ring substituent independently being alkyl. For example, B and B' can be each independently selected from substituted or unsubstituted aryl.

With further reference to Formula (Ib), each aryl substituent and each heteroaryl substituent can be each independently selected from one or more of the substituents described above. For example, B and B' can be each independently selected from substituted or unsubstituted phenyl, e.g., phenyl substituted with —(OC$_2$H$_4$)3-OH and —(OC$_2$H$_4$)3-acrylate; alkoxyphenyl, e.g., 4-methoxyphenyl and 4-butoxyphenyl; halo phenyl, e.g., 4-fluorophenyl; and morpholino phenyl, e.g., 4-morpholino phenyl.

Additionally or alternatively, the photochromic compounds of the present invention can be represented by the core skeletal structure of Formula (Ic):

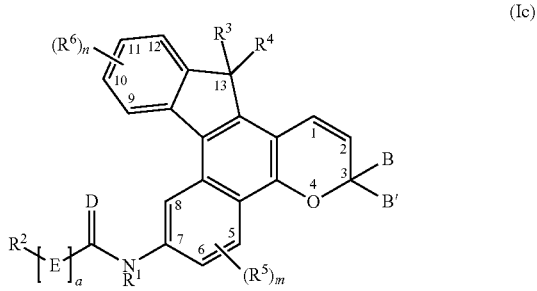

With reference to Formula (Ic), D, E, a, $R^1$, $R^2$, $R^{2'}$, $R^3$, $R^4$, B, and B' are as previously described with respect to Formulas (I) and/or (Ia) and/or (Ib).

As described above, the remaining numbered ring positions (e.g., 1 and 2) of the core skeletal structure of Formula (Ic) without a specifically shown substituent can have covalently bonded thereto hydrogen or a group other than hydrogen, for example, such as a group described herein.

With further reference to Formula (Ic), m is 0 to 3, n is 0 to 4, $R^5$ independently for each m, and $R^6$ independently for each n, are each independently selected from hydroxyl; cyano; (meth)acrylate; amino; a lengthening group $L^1$; halogen selected from fluoro, chloro, bromo, or iodo; substituted or unsubstituted alkyl; substituted or unsubstituted alkenyl; substituted or unsubstituted alkynyl; haloalkyl; perhaloalkyl; boronic ester or boronic acid; polyether, polyester, polycarbonate, or polyurethane; substituted or unsubstituted aryl; substituted or unsubstituted heterocycloalkyl; substituted or unsubstituted heteroaryl; nitrogen-containing heterocycle; or substituted or unsubstituted alkoxy, substituted or unsubstituted alkylthio, substituted or unsubstituted aryloxy, substituted or unsubstituted arylthio, ketone, aldehyde, ester, carboxylic acid, carboxylate, amide, urea, siloxane, alkoxysilane, polysiloxane, carbonate, or carbamate. For example, $R^5$ independently for each m and $R^6$ independently for each n, can be each independently selected from halogen, alkoxy, perhaloalkyl, substituted or unsubstituted aryl; aryl amino, e.g., diphenyl amino; alkyl amino, e.g., dimethyl amino; cyclic amino, e.g., morpholino, piperidino, or pyrrolidino; heteroaromatics; e.g., imidazole, pyrrole, indole, or carbazole. For example, the alkoxy can be a $C_1$-$C_6$ alkoxy.

For example, the haloalkyl can be a $C_1$-$C_{20}$ haloalkyl. For example, the perhaloalkyl can be a $C_1$-$C_{20}$ perhaloalkyl.

With further reference to Formula (Ic), each lengthening group $L^1$ can be independently represented by the following Formula (2), $$-[S_1]_c-[Q_1-[S_2]_d]_{d'}-[Q_2-[S_3]_e]_{e'}-[Q_3-[S_4]_f]_{f'}-S_5-P \quad \text{Formula (2)}$$

wherein:

(a) $Q_1$, $Q_2$, and $Q_3$ for each occurrence, are independently a divalent group selected from the group consisting of unsubstituted aryl, substituted aryl, unsubstituted heteroaryl, substituted heteroaryl, unsubstituted cycloalkyl, substituted cycloalkyl, unsubstituted heterocycloalky, or substituted heterocycloalkyl;

wherein the aryl substituents, heteroaryl substituents, cycloalkyl substituents, and heterocycloalkyl substituents are each independently selected from the group consisting of P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_3$-$C_{10}$ cycloalkoxy, or alkyl;

(b) c, d, e, and f are each independently chosen from an integer of 1 to 20; and each $S_1$, $S_2$, $S_3$, $S_4$, and $S_5$ is independently chosen for each occurrence from a spacer unit selected from the group consisting of:

(i) alkylene, substituted alkylene, haloalkylene, substituted haloalkylene, —Si(CH$_2$)$_g$—, and —Si[(CH$_3$)$_2$]O)$_h$—, wherein g for each occurrence is independently chosen from an integer from 1 to 20; h for each occurrence is independently chosen from an integer from 1 to 16; and the substituents for the alkylene and haloalkylene are independently selected from the group consisting of alkyl or aryl;

(ii) —N(Z)—, —C(Z)=C(Z)—, —C(Z)=N—, —C(Z')$_2$—C(Z')$_2$—, —N(Z)—C(Z)$_2$-, and a single bond, wherein Z for each occurrence is independently selected from the group consisting of hydrogen, alkyl or aryl, and Z' for each occurrence is independently selected from the group consisting of alkyl or aryl; or (iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1$-$C_{24}$ alkylene residue, the $C_1$-$C_{24}$ alkylene residue being unsubstituted, mono-substituted by cyano or halogen, or poly-substituted by halogen, provided that when two spacer units comprising heteroatoms are linked together the spacer units are linked so that heteroatoms are not directly linked to each other;

(c) P is hydrogen; and (d) d', e' and f' are each independently chosen from 0, 1, 2, 3, and 4, provided that the sum of d'+e'+f' is at least 1.

For example, $R^6$ can be a lengthening group $L^1$ at the 10-position.

With further reference to Formula (Ic), each alkyl substituent, each aryl substituent, each heterocycloalkyl substituent, and each heteroaryl substituent, can be in each case independently selected from one or more of the substituents described above. Further, $R^5$ can be a halo group at the 5-position, e.g., a fluoro group; or $R^5$ can be an alkoxy group at the 6-position, e.g., methoxy. Further, $R^6$ can be a di-trifluoromethyl group at the 10- and/or 12-positions; or $R^6$ can be trifluoromethyl, phenyl, methoxy, or alkylthio at the 11-position.

As used herein, the term "polysiloxane" such as with regard to substituents of various groups of the photochromic compounds of the present invention, includes a material represented by the following Formula (G):

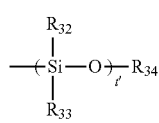

(G)

With reference to Formula (G), subscript t' is from 2 to 200, such as from 2 to 100, or 2 to 50, or from 2 to 25, or from 2 to 15, or from 2 to 10, or from 2 to 5, in each case inclusive of the recited values. With further reference to Formula (G): $R_{32}$ and $R_{33}$, for each t', are each independently selected from alkyl or aryl; and $R_{34}$ is selected from hydrogen, alkyl, or aryl. With some embodiments: $R_{32}$ and $R_{33}$ for each t', are each independently selected from methyl, ethyl, or phenyl; and $R_{34}$ is selected from hydrogen, methyl, ethyl, or phenyl.

As used herein, the term "polysiloxane" such as with regard to substituents of various groups of the photochromic compounds of the present invention, alternatively to or in addition to a material represented by Formula (G), includes a material represented by the following Formula (H):

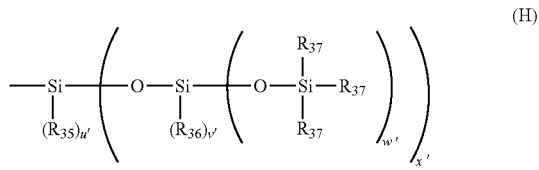

(H)

With reference to Formula (H), subscript u' is 0-2 and subscript x' is 1-3, provided that u'+x' is 3; and subscript v' is 0-2 and subscript w' is 1-3, provided that v'+w' is 3. With further reference to Formula (H), $R_{35}$ independently for each u', $R^{36}$ independently for each v' and each x', and each $R_{37}$ independently for each w' and each x', are in each case independently selected from alkyl (such as, but not limited to, methyl or ethyl) or aryl (such as, but not limited to, phenyl). With some embodiments, the photochromic compounds of the present invention, such as those described with reference to Formulas (I), (Ia), (Ib), and/or (Ic) can each be used alone, or in combination with one or more other photochromic compounds. For example, the photochromic compounds of the present invention can be used in conjunction with one or more other photochromic compounds having activated absorption maxima within the range of 300 to 1,000 nanometers. Further, the photochromic compounds according to the present invention can be used in conjunction with one or more complementary conventional polymerizable or compatiblized photochromic compounds, such as for example, those disclosed in U.S. Pat. No. 6,113,814 (at col. 2, line 39 to col. 8, line 41), and U.S. Pat. No. 6,555,028 (at col. 2, line 65 to col. 12, line 56).

The photochromic compounds of the present invention can be used in combination with a mixture of other photochromic compounds. For example, although not limiting herein, mixtures of photochromic compounds can be used to attain certain activated colors, such as a near neutral gray or near neutral brown. See, for example, U.S. Pat. No. 5,645,767, col. 12, line 66 to col. 13, line 19, which describes the parameters that define neutral gray and brown colors.

Examples of classes of other photochromic compounds that can be used in combination with the photochromic compounds of the present invention, include, but are not limited to, indeno-fused naphthopyrans, naphtho[1,2-b]pyrans, naphtho[2,1-b]pyrans, spirofluoroeno[1,2-b]pyrans, phenanthrenopyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof. Further examples of other photochromic compounds that can be used in combination with the photochromic compounds of the present invention include, but are not limited to, those disclosed at column 34, line 20 through column 35, line 13 of U.S. Pat. No. 9,028,728 B2.

Figure 2:
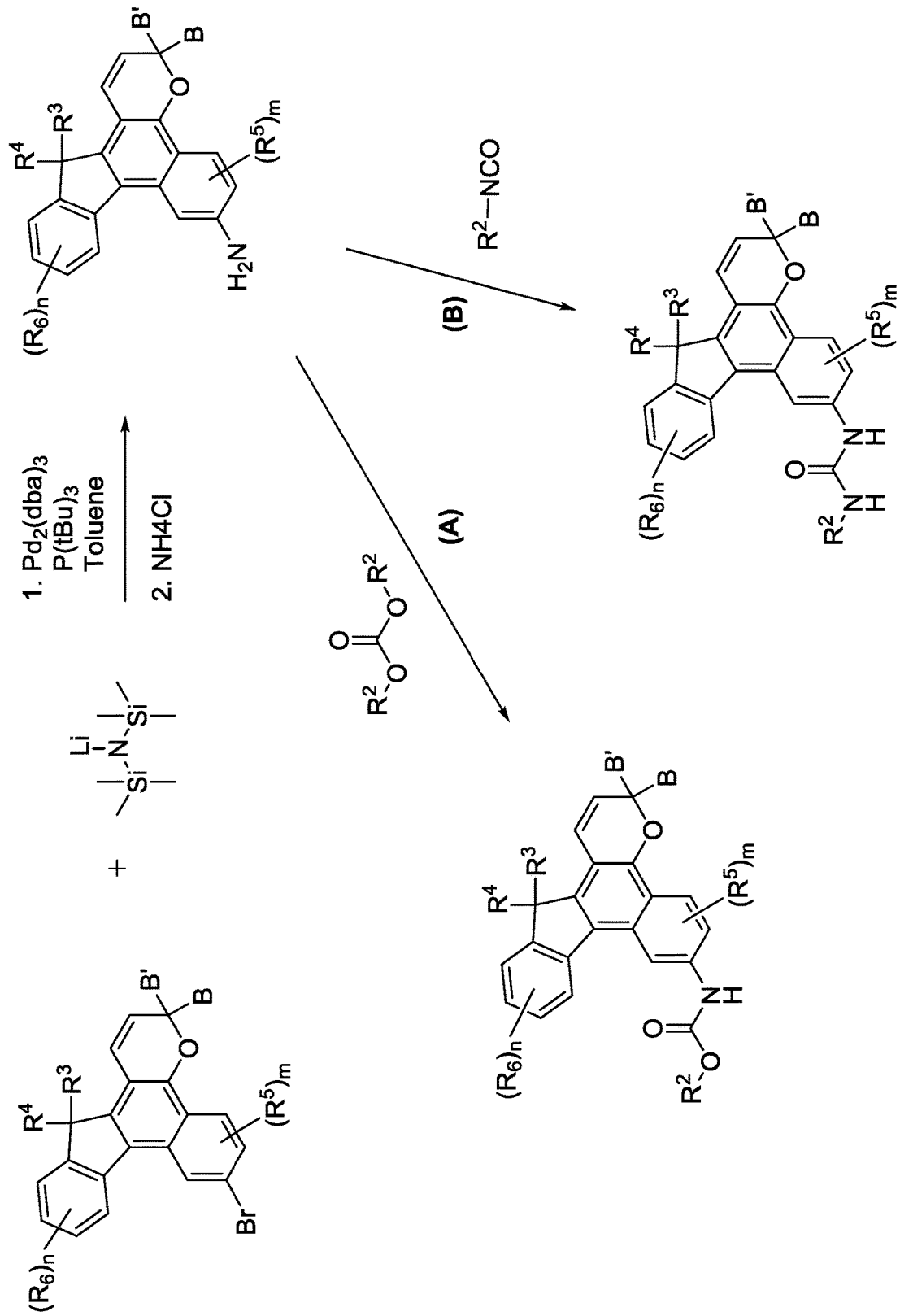
FIG. 2 illustrates a general scheme, Scheme 2, of another exemplary method for preparing photochromic compounds of the invention.

Photochromic compounds according to the present invention can be prepared in accordance with art-recognized methods. For purposes of non-limiting illustration and with reference to FIGS. 1 and 2, general synthetic schemes, Schemes 1 and 2, for the preparation of photochromic compounds according to the present invention is described as follows. Further detailed descriptions of the preparation of photochromic compounds of the present invention are provided further herein in the Examples. In FIGS. 1 and 2, the various groups, such as D, E, a, $R^1$, $R^2$, $R^{2'}$, $R^3$, $R^4$, $R^5$, $R^6$, B, and B', and related subscripts, such as m and n, of the various intermediates, reactants, and/or compounds depicted, are each as described previously herein, and/or represent precursors of such groups.

FIG. 1 illustrates a cross coupling reaction catalyzed with various palladium source and ligand combinations to convert aryl halides, triflates, or tosylates to an amide group. For example, see the publication Ikawa, et al. J. Am. Chem. Soc., 2007, 129, 13007.

FIG. 2 illustrates that an aryl-$NH_2$ group can be made by converting the aryl-bromide group to a (bis)trimethylsilyl amine group using palladium cross coupling conditions followed by hydrolysis to the amino group with acid. For example see the publication Fee, et al., Org. Lett., 2001, 3, 2729.

The conversion from the aryl-$NH_2$ group to the carbamate (Path A) can be accomplished by reacting the aryl-$NH_2$ with dialkyl carbonate. For example see Tundo, et al. J. Org. Chem., 2005, 70, 2219.

The conversion of the aryl-$NH_2$ group to the aryl-urea group (Path B) can be accomplished by reaction of the aryl-$NH_2$ with a substituted isocyanate group. This reaction can be catalyzed by typical urethane catalysts, such as dibutyltin dilaurate or trialkyl amines.

In accordance with the present invention there is also provided a photochromic composition, which includes at least one photochromic compound according to the present invention, such as those represented by Formula (I), (Ia), (Ib), or (Ic), as described previously herein.

The photochromic composition can include: (i) an organic material, in which the organic material is at least one of a polymeric material, an oligomeric material, or a monomeric material; and (ii) a photochromic compound according to the present invention, which is incorporated into at least a portion of the organic material. The photochromic compound can be incorporated into a portion of the organic material by methods including, but not limited to, at least one of blending or bonding the photochromic compound with the organic material or a precursor of the organic material. As used herein with reference to the incorporation of photochromic compounds into an organic material, the terms "blending" and "blended" mean that the photochromic compound/material is intermixed or intermingled with the at least a portion of the organic material, but not bonded to the organic material. Further, as used herein with reference to the incorporation of photochromic compounds into an organic material, the terms "bonding" or "bonded" mean that the photochromic compound/material is linked, such as by one or more covalent bonds, to a portion of the organic material or a precursor thereof. For example, although not limiting herein, the photochromic material can be linked to the organic material through a reactive substituent.

When the organic material is a polymeric material, the photochromic compound can be incorporated into at least a portion of the polymeric material or at least a portion of the monomeric material or oligomeric material from which the polymeric material is formed. For example, photochromic compound(s) according to the present invention that have a reactive substituent can be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process.

As discussed above, the photochromic compositions according to present invention can include an organic material chosen from a polymeric material, an oligomeric material and/or a monomeric material, with some embodiments. Examples of polymeric materials that can be used with the photochromic compositions of the present invention include, but are not limited to: poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl (meth)acrylamide functional polymers; poly(siloxane); poly(silane); and combinations and mixtures thereof. Further classes and examples of polymeric materials that can be used with the photochromic compositions of the present invention include, but are not limited to, those disclosed at column 39, line 45 through column 40, line 67 of U.S. Pat. No. 9,028,728 B2.

The photochromic composition of the present invention can include at least one of, a complementary photochromic material (including one or more of those other photochromic materials and compounds described previously herein), a photoinitiator, a thermal initiator, a polymerization inhibitor, a solvent, a light stabilizer, a heat stabilizer, a mold release agent, a rheology control agent, a leveling agent, a free radical scavenger, and/or an adhesion promoter.

The photochromic composition according to the present invention can be a photochromic coating composition. Photochromic coating compositions of the present invention can include: a photochromic compound according to the present invention, such as described previously herein with regard to Formula (I), (Ia), (Ib), or (Ic); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. The photochromic coating composition can be a curable or thermosetting coating composition.

The curable resin composition of the curable photochromic coating compositions according to the present invention can include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance, and hardness.

Examples of curable resin compositions that can be used with the curable photochromic coating compositions according to the present invention include, but are not limited to: curable resin compositions including epoxide functional polymer (e.g., (meth)acrylic polymers containing residues of glycidyl (meth)acrylate) and epoxide reactive crosslinking agent (e.g., containing active hydrogens, such as hydroxyls, thiols and amines); and curable resin compositions including active hydrogen functional polymer (e.g., hydroxy, thiol, and/or amine functional polymer) and capped (or blocked) isocyanate functional crosslinking agent. By "capped (or blocked) isocyanate functional crosslinking agent" is meant a crosslinking agent having two or more capped isocyanate groups that can decap (or deblock) under cure conditions (e.g., at elevated temperature) to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer). Further examples of curable resin compositions that can be used with the curable photochromic coating compositions according to the present invention include, but are not limited to, those disclosed in: paragraphs [0176] through [0190] of WO 2016/142496 A1; and paragraphs [0005], [0037] through [0051], [0056] through [0059], and [0063] through [0065] of WO 2017/030545 A1.

Curable photochromic coating compositions according to the present invention can, optionally, contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from BASF under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic compounds of the present invention can be used in amounts (or ratios) such that the compositions, organic material or substrate (e.g., photochromic articles and photochromic coatings) into which the photochromic compounds are incorporated or otherwise connected exhibits desired optical properties. The amount and types of photochromic material can be selected such that the composition, organic material or substrate is clear or colorless when the photochromic compound is in the closed-form (e.g., in the bleached or unactivated state), and can exhibit a desired resultant color when the photochromic compound (such as a photochromic indeno-fused naphthopyran of the present invention) is in the open-form (e.g., when activated by actinic radiation). The precise amount of the photochromic material that is utilized in the various photochromic compositions and articles described herein is not critical provided that a sufficient amount is used to produce the desired effect. The particular amount of the photochromic material used can depend on a variety of factors, such as but not limited to, the absorption characteristics of the photochromic compound, the color and intensity of the color desired upon activation, and the method used to incorporate or connect the photochromic material to the substrate. Photochromic compositions according to the present invention can include the photochromic compound according to the present invention, including the compounds represented by Formula (I), (Ia), (Ib), or (Ic) in an amount of from 0.01 to 40 weight percent, such as from 0.05 to 15 weight percent, such as from 0.1 to 5 weight percent, based on the weight of the photochromic composition. For purposes of further non-limiting illustration, the amount of the photochromic compound/material including the compounds represented by Formula (I), (Ia), (Ib), or (Ic) that is incorporated into an organic material can range from 0.01 to 40 weight percent, such as from 0.05 to 15 weight percent, such as from 0.1 to 5 weight percent, based on the weight of the organic material.

The present invention also relates to photochromic articles that include one or more photochromic compounds according to the present invention, such as represented by Formula (I), (Ia), (Ib), or (Ic). The photochromic articles can be prepared by art-recognized methods, such as by imbibition methods, cast-in-place methods, coating methods, in-mold coating methods, over-mold methods, and lamination methods.

For example, the photochromic articles can be selected from ophthalmic articles, display articles, windows, mirrors, active liquid crystal cell articles, and passive liquid crystal cell articles.

For example, the photochromic articles of the present invention can be ophthalmic articles, and the ophthalmic articles can be selected from corrective lenses, non-corrective lenses, contact lenses, intra-ocular lenses, magnifying lenses, protective lenses, and visors.

For example, the photochromic articles of the present invention can be display articles, and the display articles can be selected from screens, monitors, and security elements.

The present invention is more particularly described in the following examples, which are intended as illustrative only, since numerous modifications and variations therein will be apparent to those skilled in the art.

EXAMPLES

The following examples are provided to illustrate photochromic compounds of the invention, particularly the improvement in temperature dependence of photochromic compounds of the invention. Part 1 provides descriptions of the synthesis of photochromic compounds of the invention. Part 2 provides an evaluation of the photochromic performance of the photochromic compounds of the invention versus comparative photochromic compounds.

Part 1: Synthesis of Photochromic Compounds

Example 1

Step 1.
2-Bromo-9-phenyl-7,7-dipropyl-7H-benzo[c]fluoren-5-ol (5.0 g) was added to a round bottom flask containing 100 mL of $CH_2Cl_2$ with stirring, followed by addition of p-toluenesulfonic acid (0.2 g). A solution of 1,1-bis(4-butoxyphenyl)prop-2-yn-1-ol (4.1 g in 25 mL $CH_2Cl_2$) was slowly added to the reaction mixture and heated to reflux. After three hours, additional 1,1-bis(4-butoxyphenyl)prop-2-yn-1-ol (0.5 g in 10 mL $CH_2Cl_2$) was added. After an additional hour at reflux, the solution was cooled to room temperature, and was passed through a silica plug using $CH_2Cl_2$ as eluent, then concentrated under vacuum. Crystallization from ethyl acetate/hexanes/methanol gave an 81% yield of 7-bromo-3,3-bis(4-butoxyphenyl)-11-phenyl-13,13-dipropyl-3,13-dihydrobenzo[h]indeno[2,1-f]chromene, as confirmed by $^1H$ NMR.

Step 2.
The product of step 1 above (3.0 g) and benzamide (0.68 g) were added under $N_2$ atmosphere into a two-neck round bottom flask containing 100 mL toluene and ethanol (9:1 v/v). To this was added $Cs_2CO_3$ (4.8 g) and 4,5-Bis(diphenylphosphino)-9,9-dimethylxanthene (Xantphos) (0.54 g) with stirring. The solution was sparged with nitrogen for 10 minutes. Tris(dibenzylideneacetone)dipalladium(0) (0.35 g) was added and the mixture was heated to reflux. After two hours of reflux the reaction mixture was cooled to room temperature then added to ice-cold water. The pH was adjusted to pH<7 using concentrated HCl, followed by extraction with ethyl acetate (EtOAc). The organic layer was concentrated, dissolved in 50 mL $CH_2Cl_2$ and dried over anhydrous $MgSO_4$. The solution was passed through a short silica plug using EtOAc/Hexanes (1:2) as eluent. The desired fraction was collected, concentrated, and precipitated from methanol to give a product with the structure shown in Table 3.

Additional photochromic dyes were prepared according to the procedure for Example 1. For each example, an appropriately substituted benzo[c]fluoren-5-ol was used in place of 2-bromo-9-phenyl-7,7-dipropyl-7H-benzo[c]fluoren-5-ol in Step 1, as indicated in Table 1 to give the desired substitution pattern in the final product. Also, the 1,1-bis(4-butoxyphenyl)prop-2-yn-1-ol of Step 1 was replaced with an equimolar amount of the 1,1-disubstituted prop-2-yn-1-ol ("propargyl alcohol") indicated in the "Step 1" column according to Table 2. Further, the benzamide of Example 1, Step 2, was replaced with an equimolar amount of the amide indicated in the "Amide" column according to Table 1.

TABLE 1

Reaction components for Examples 2-23

| No. | substituted benzo[c]fluoren-5-ol | Propargyl alcohol | Amide |
|---|---|---|---|
| Example 2 | 2-bromo-9-phenyl-7,7-dipropyl-7H-benzo[c]fluoren-5-ol | HO-C(C≡CH)(4-BuO-C6H4)(4-BuO-C6H4) | acetamide |
| Example 3 | 2-bromo-9-phenyl-7,7-dipropyl-7H-benzo[c]fluoren-5-ol | HO-C(C≡CH)(4-BuO-C6H4)(4-BuO-C6H4) | 4-(trifluoromethyl)benzamide |
| Example 4 | 2-bromo-9-phenyl-7,7-dipropyl-7H-benzo[c]fluoren-5-ol | HO-C(C≡CH)(4-BuO-C6H4)(4-BuO-C6H4) | 4-methoxybenzamide |
| Example 5 | 2-bromo-9-phenyl-7,7-dipropyl-7H-benzo[c]fluoren-5-ol | HO-C(C≡CH)(4-BuO-C6H4)(4-BuO-C6H4) | 4-(dimethylamino)benzamide |
| Example 6 | 2-bromo-9-phenyl-7,7-dipropyl-7H-benzo[c]fluoren-5-ol | HO-C(C≡CH)(4-BuO-C6H4)(4-BuO-C6H4) | 2-methylbenzamide |
| Example 7 | 2-bromo-9-phenyl-7,7-dipropyl-7H-benzo[c]fluoren-5-ol | HO-C(C≡CH)(4-MeO-C6H4)(4-MeO-C6H4) | benzamide |
| Example 8 | 2-bromo-9-phenyl-7,7-dipropyl-7H-benzo[c]fluoren-5-ol | HO-C(C≡CH)(4-F-C6H4)(4-morpholino-C6H4) | acetamide |
| Example 9 | 2-bromo-7,7-dimethyl-9-phenyl-7H-benzo[c]fluoren-5-ol | HO-C(C≡CH)(4-MeO-C6H4)(4-MeO-C6H4) | benzamide |
| Example 10 | 2-bromo-7,7-dipropyl-7H-benzo[c]fluoren-5-ol | HO-C(C≡CH)(4-MeO-C6H4)(4-MeO-C6H4) | benzamide |

TABLE 1-continued

Reaction components for Examples 2-23

| No. | substituted benzo[c]fluoren-5-ol | Propargyl alcohol | Amide |
|---|---|---|---|
| Example 11 | 2-bromo-7,7-dipropyl-7H-benzo[c]fluoren-5-ol | bis(4-methoxyphenyl) propargyl alcohol | acetamide |
| Example 12 | 2-bromo-9-methoxy-7,7-dipropyl-7H-benzo[c]fluoren-5-ol | bis(4-butoxyphenyl) propargyl alcohol | benzamide |
| Example 13 | 2-bromo-9-methoxy-7,7-dimethyl-7H-benzo[c]fluoren-5-ol | piperazine-functionalized propargyl alcohol with methacrylate ester | acetamide |
| Example 14 | 2-bromo-9-(methylthio)-7,7-dipropyl-7H-benzo[c]fluoren-5-ol | bis(4-methoxyphenyl) propargyl alcohol | benzamide |
| Example 15 | 2-bromo-7,7-dimethyl-9-(trifluoromethyl)-7H-benzo[c]fluoren-5-ol | (4-methoxyphenyl)(4-butoxyphenyl) propargyl alcohol | benzamide |
| Example 16 | 2-bromo-7,7-dimethyl-9-(trifluoromethyl)-7H-benzo[c]fluoren-5-ol | (4-methoxyphenyl)(4-butoxyphenyl) propargyl alcohol | acetamide |
| Example 17 | 2-bromo-7,7-dimethyl-9-(trifluoromethyl)-7H-benzo[c]fluoren-5-ol | (4-methoxyphenyl)(4-butoxyphenyl) propargyl alcohol | 4-(trifluoromethyl)benzamide |
| Example 18 | 2-bromo-7,7-dimethyl-9-(trifluoromethyl)-7H-benzo[c]fluoren-5-ol | (4-methoxyphenyl)(4-butoxyphenyl) propargyl alcohol | 4-methoxybenzamide |
| Example 19 | 2-bromo-7,7-dimethyl-9-(trifluoromethyl)-7H-benzo[c]fluoren-5-ol | (4-methoxyphenyl)(4-butoxyphenyl) propargyl alcohol | 4-(dimethylamino)benzamide |

TABLE 1-continued

Reaction components for Examples 2-23

| No. | substituted benzo[c]fluoren-5-ol | Propargyl alcohol | Amide |
|---|---|---|---|
| Example 20 | 2-bromo-7,7-dimethyl-9-(trifluoromethyl)-7H-benzo[c]fluoren-5-ol | HO, ≡, with MeO-phenyl and OBu-phenyl substituents | 2-methylbenzamide |
| Example 21 | 2-bromo-7,7-dimethyl-9-(trifluoromethyl)-7H-benzo[c]fluoren-5-ol | HO, ≡, with MeO-phenyl and OBu-phenyl substituents | 2-methoxybenzamide (OMe) |
| Example 22 | 2-bromo-7,7-dimethyl-9-(trifluoromethyl)-7H-benzo[c]fluoren-5-ol | HO, ≡, with MeO-phenyl and OBu-phenyl substituents | 2-hydroxybenzamide (OH) |
| Example 23 | 2-bromo-7,7-dimethyl-9-(trifluoromethyl)-7H-benzo[c]fluoren-5-ol | HO, ≡, with phenyl and OBu-phenyl substituents | benzamide |

Examples 24-26

Example 24

Step 1.

3-Methoxy-7,7-dimethyl-8,10-bis(trifluoromethyl)-7H-benzo[c]fluorene-2,5-diol (10.0 g) was added to a round bottom flask containing 200 mL of $CH_2Cl_2$ under nitrogen and warmed to 40° C. until fully dissolved. p-Toluenesulfonic acid (0.044 g) was then added. A solution of 1-(4-methoxyphenyl)-1-phenylprop-2-yn-1-ol (5.5 g) in 25 mL $CH_2Cl_2$ was added slowly to the reaction mixture at 40° C. with stirring, then heated at reflux overnight. The reaction mixture was washed with aqueous $NaHCO_3$ solution and dried over anhydrous $MgSO_4$. After removal of solvent under vacuum, the residue was combined with a minimal volume of $CH_2Cl_2$ and then passed through a silica gel plug with $CH_2Cl_2$ eluent. Then solvent was removed and the product was crystallized from diethyl ether. The product was characterized by NMR as 6-methoxy-3-(4-methoxyphenyl)-13,13-dimethyl-3-phenyl-10,12-bis(trifluoromethyl)-3,13-dihydrobenzo[h]indeno[2,1-f]chromen-7-ol. Yield was 82%.

Step 2.

The product of Step 1 above (10.0 g; 0.015 mol) was dissolved in 150 mL of $CH_2Cl_2$ followed by addition of triethylamine (4.6 g) was added with stirring. Trifluoromethanesulfonic anhydride (5.08 g) was added dropwise with stirring under nitrogen at ice cold temperature. Once the addition was complete the reaction was brought to room temperature and stirred for one hour. The solution was concentrated and passed through a silica gel plug. Solvent was removed and the residue was washed with hexanes. The product was characterized by NMR as 6-methoxy-3-(4-methoxyphenyl)-13,13-dimethyl-3-phenyl-10,12-bis(trifluoromethyl)-3,13-dihydrobenzo[h]indeno[2,1-f]chromen-7-yl trifluoromethanesulfonate. Yield was 85%.

Step 3.

The product of step 2 above (0.5 g) and benzamide (0.11 g) were added under nitrogen into a two-neck round bottom flask containing 50 mL toluene and EtOH (9:1 v/v) with a magnetic stirrer. Then $Cs_2CO_3$ (0.8 g) and Xanthphos (0.09 g) were added with stirring. The solution was sparged with nitrogen for 10 minutes followed by addition of tris(dibenzylideneacetone)dipalladium(0) (0.06 g) then heating to reflux. After 2 hours at reflux, the reaction was cooled to room temperature then added to ice-cold water. The pH was adjusted to less than 7 using concentrated HCl. The mixture was extracted with EtOAc, and the organic layer concentration by evaporation. The residual mass was dissolved in 50 mL of $CH_2Cl_2$, dried over anhydrous $MgSO_4$, and passed through a short silica gel plug using EtOAc/Hexanes (1:2) as eluent. The desired fraction was collected, concentrated, and the product was precipitated from methanol to yield solid product with the structure shown in Table 3.

Additional photochromic dyes were prepared according to the procedure for Example 24. For each example, an appropriately substituted benzo[c]fluoren-5-ol was used in place of 2-bromo-9-phenyl-7,7-dipropyl-7H-benzo[c]fluoren-5-ol in Step 1, as indicated in Table 1 to give the desired substitution pattern in the final product. Also, the 1-(4-methoxyphenyl)-1-phenylprop-2-yn-1-ol of Step 1 was replaced with an equimolar amount of the 1,1-disubstituted prop-2-yn-1-ol ("propargyl alcohol") indicated in the "Step 1" column according to Table 2. Further, the benzamide of Example 24, Step 3, was replaced with an equimolar amount of the amide indicated in the "Amide" column according to Table 2.

TABLE 2

Reaction components for Examples 25-26

| No. | Substituted benzo[c]fluoren-5-ol | Propargyl alcohol | Amide |
|---|---|---|---|
| Example 25 | 3-methoxy-7,7-dimethyl-7H-benzo[c]fluorene-2,5-diol | *[structure: HO-C(C≡CH) with two 4-BuO-phenyl groups]* | *[benzamide structure]* |
| Example 26 | 3-methoxy-7,7-dimethyl-9-phenyl-7H-benzo[c]fluorene-2,5-diol | *[structure: HO-C(C≡CH) with two 4-BuO-phenyl groups]* | *[benzamide structure]* |

Example 27

The product of Example 24 (1.0 g) was dissolved in 25 mL tetrahydrofuran (THF) under nitrogen then immersed into an ice-water bath. To this was added n-BuLi (1.6 M in hexanes)(1 0.0 mL) and the mixture stirred for 10 minutes, after which methyl iodide (0.22 g; 0.1 mL) was added. The reaction mixture was removed from the ice bath and stirred for an hour at room temperature then poured into water, adjusted to pH<7 with dilute HCl then extracted with EtOAc. Solvent was removed and the residue was run through a silica gel plug using Hexanes and 20% EtOAc over 30 minutes. The product was confirmed by NMR as having a structure consistent with the N-methyl amide shown in Table 3.

Example 28

The procedure of Example 27 was followed using the product of Example 23 in place of the product of Example 24.

Example 29

Step 1.

2-Bromo-9-phenyl-7,7-dipropyl-7H-benzo[c]fluoren-5-ol (2.50 g; 3.46 mmol) was added to a three-neck round bottom flask containing 100 mL toluene under a nitrogen blanket at room temperature. The solution was sparged with nitrogen for five minutes, then 1M lithium bis(trimethylsilyl) amide in THF (17.3 mL; 17.3 mmol) and Bis(dibenzylideneacetone)palladium(0) (0.199 g; 0.346 mmol) were added followed by 1M Tri-tert-butylphosphine in Toluene (0.242 mL; 0.242 mmol). After thirty minutes at room temperature, the reaction mixture was poured into water followed by addition of saturated ammonium chloride with vigorous stirring. The solution was extracted with ethyl acetate and the organic layer dried over anhydrous NaSO$_4$, filtered, and solvent removed by evaproation. The residue was passed through a CombiFlash® Rf column (commercially available from Teledyne Isco) with EtOAc/Hexanes (1:4) as the eluent. The desired fraction was collected, concentrated and recrystallized from hexanes and methanol to give 3,3-bis(4-methoxyphenyl)-11-phenyl-13,13-dipropyl-3,13-dihydrobenzo[h]indeno[2,1-f]chromen-7-amine. Yield was 78%.

Step 2.

The product of Step 1 above (0.800 g; 1.22 mmol) was added to a 20 mL vial containing Dimethyl Carbonate (4.38 g; 48.6 mmol) and Potassium tert-butoxide (0.164 g; 1.5 mmol) with stirring. Using a hot plate, the reaction was heated to boiling for eight minutes and then the vial was removed from the heat source. After extraction with ethyl acetate, the solution was dried over anhydrous NaSO$_4$, filtered, and solvent removed by evaporation. The residue was passed through a CombiFlash® Rf column (commercially available from Teledyne Isco) with EtOAc/Hexanes (1:4) as the eluent. The product was recrystallized from hexanes and methanol to give the corresponding carbamate product shown in Table 3.

Example 30

The procedure of Example 29 was followed using 2-bromo-9-methoxy-7,7-dipropyl-7H-benzo[c]fluoren-5-ol in place of 2-Bromo-9-phenyl-7,7-dipropyl-7H-benzo[c]fluoren-5-ol to yield the corresponding carbamate shown in Table 3.

Example 31

The product of Step 1, Example 29 (0.40 g; 0.608 mmol) was added to a reaction flask containing 10 mL of dichloromethane and Hexyl isocyanate (0.092 g; 0.73 mmol) with stirring followed by addition of one diluted drop of tributyl tin dilaurate. The solution was stirred for ten minutes at room temperature at which time a precipitate formed in the flask. This precipitate was collected and identified as the corresponding urea shown in Table 3.

The final products of Examples 1-31 are summarized in Table 3, with the yield of the final step and characterization method(s).

TABLE 3

Summary of Examples

| Example | Structure | Yield[1] (%) | Characterization 1 = $^1$H NMR 2 = mass spec |
|---|---|---|---|
| Example 1 | 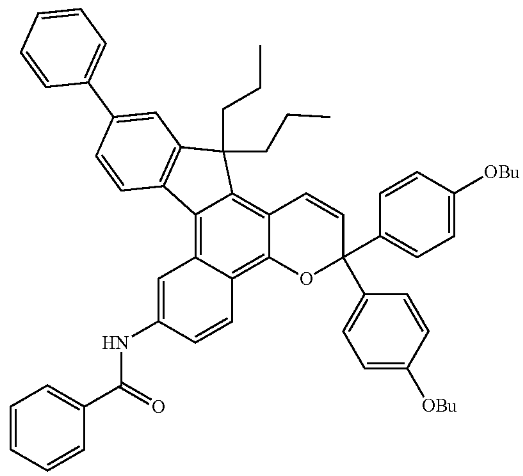 | 72 | 1, 2 |
| Example 2 | 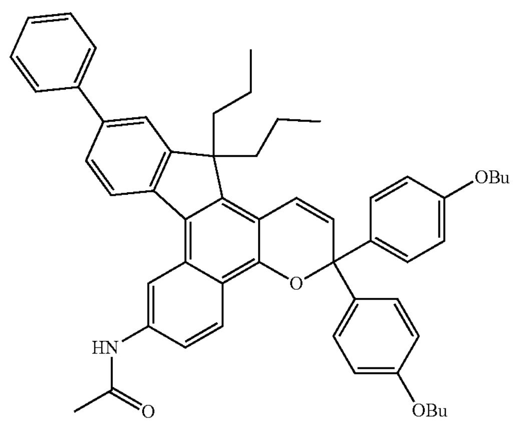 | 71 | 1, 2 |
| Example 3 | 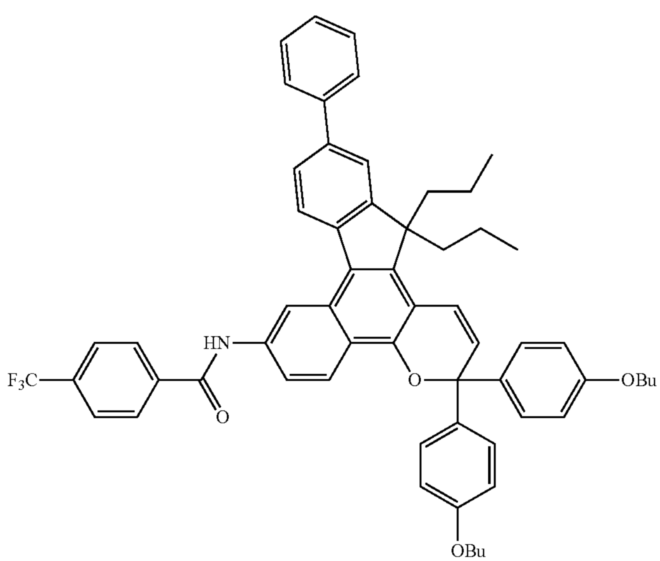 | 75 | 1, 2 |

TABLE 3-continued
Summary of Examples
| Example | Structure | Yield[1] (%) | Characterization 1 = $^1$H NMR 2 = mass spec |
|---|---|---|---|
| Example 4 | 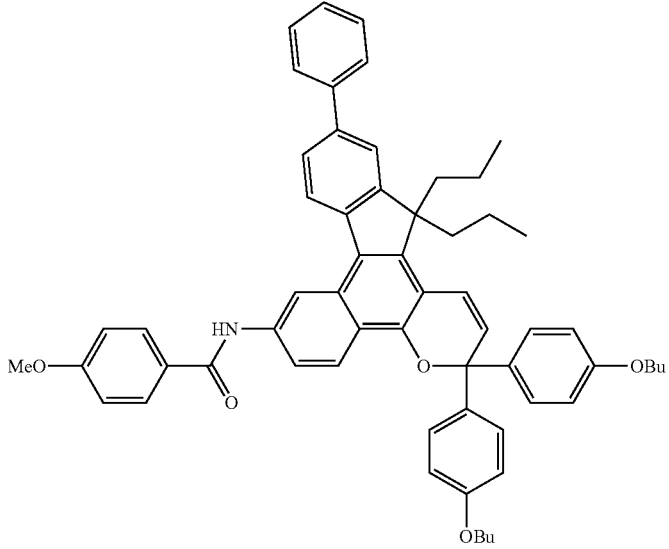 | 68 | 1, 2 |
| Example 5 | 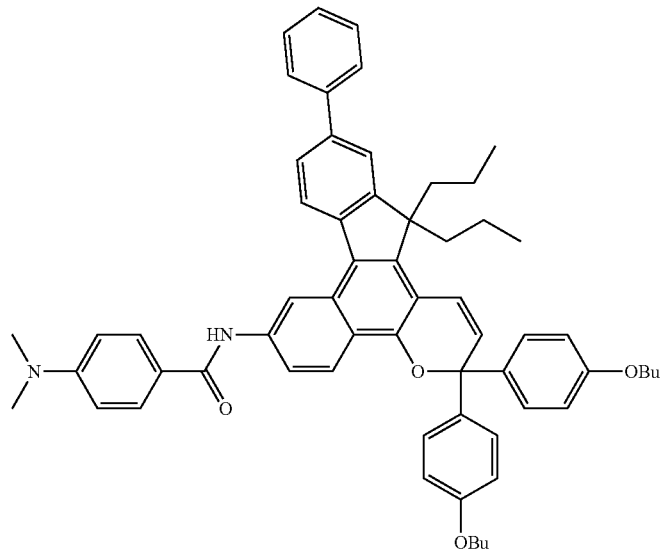 | 65 | 1, 2 |

TABLE 3-continued

Summary of Examples

| Example | Structure | Yield[1] (%) | Characterization 1 = $^1$H NMR 2 = mass spec |
|---|---|---|---|
| Example 6 | 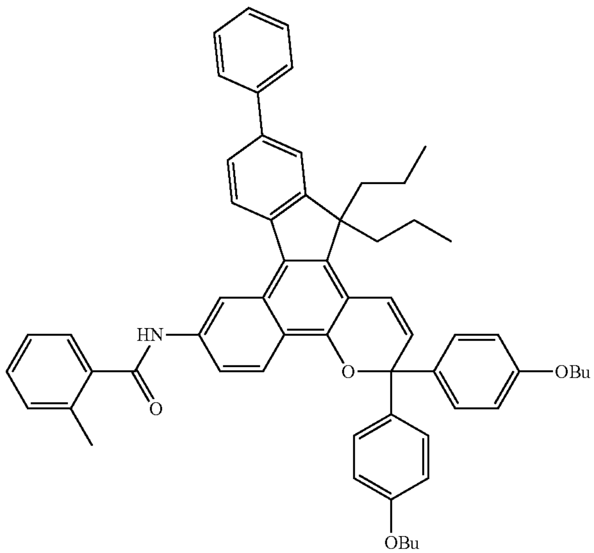 | 70 | 1, 2 |
| Example 7 | 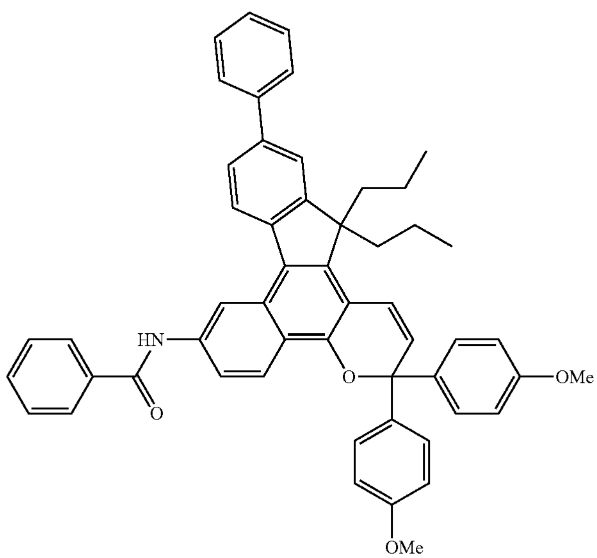 [SMILES: CCCC1(CCC)c2cc(-c3ccccc3)ccc2-c2c1c1c(c3ccc(NC(=O)c4ccccc4)cc23)OC(c2ccc(OC)cc2)(c2ccc(OC)cc2)C=C1] | 75 | 1, 2 |
| Example 8 | 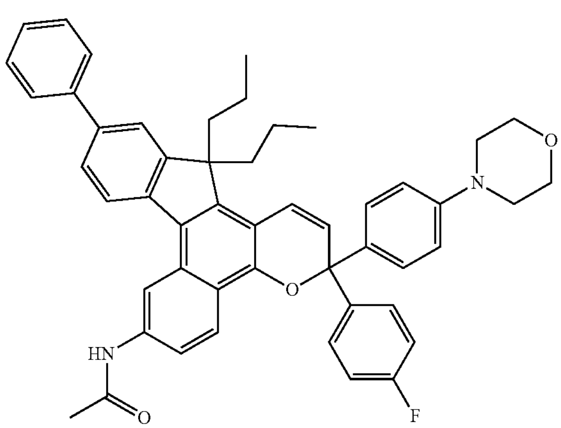 [SMILES: CCCC1(CCC)c2cc(-c3ccccc3)ccc2-c2c1c1c(c3ccc(NC(C)=O)cc23)OC(c2ccc(F)cc2)(c2ccc(N3CCOCC3)cc2)C=C1] | 65 | 1, 2 |

TABLE 3-continued
Summary of Examples
| Example | Structure | Yield[1] (%) | Characterization 1 = $^1$H NMR 2 = mass spec |
|---|---|---|---|
| Example 9 | 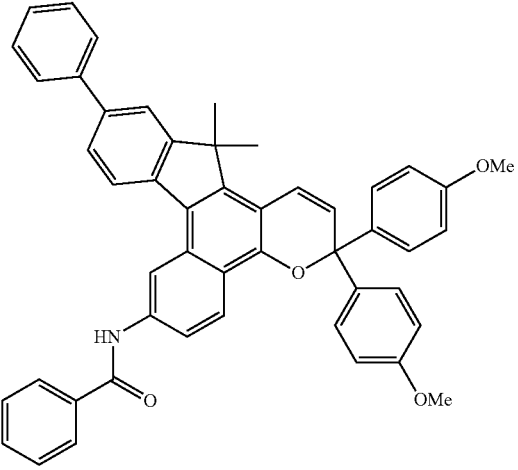 [SMILES: COc1ccc(C2(c3ccc(OC)cc3)C=Cc3c4c(c5cc(NC(=O)c6ccccc6)ccc5c3O2)-c2ccc(-c3ccccc3)cc2C4(C)C)cc1] | 63 | 1, 2 |
| Example 10 | 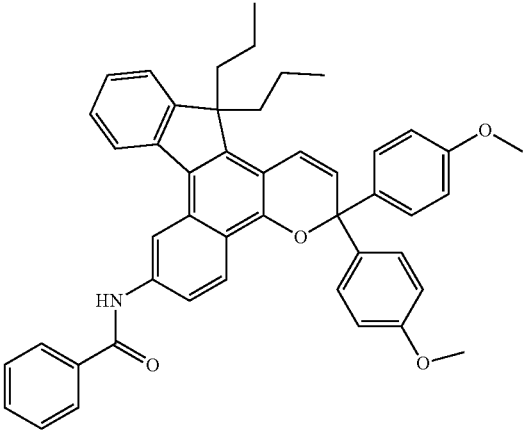 [SMILES: CCCC1(CCC)c2ccccc2-c2c1c1c(c3ccc(NC(=O)c4ccccc4)cc23)OC(c2ccc(OC)cc2)(c2ccc(OC)cc2)C=C1] | 62 | 1, 2 |
| Example 11 | 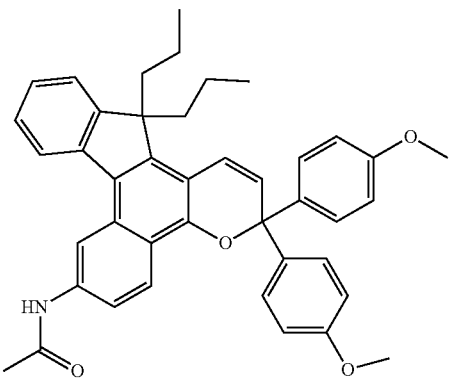 [SMILES: CCCC1(CCC)c2ccccc2-c2c1c1c(c3ccc(NC(C)=O)cc23)OC(c2ccc(OC)cc2)(c2ccc(OC)cc2)C=C1] | 65 | 1, 2 |

TABLE 3-continued

Summary of Examples

| Example | Structure | Yield[1] (%) | Characterization 1 = $^1$H NMR 2 = mass spec |
|---|---|---|---|
| Example 12 | 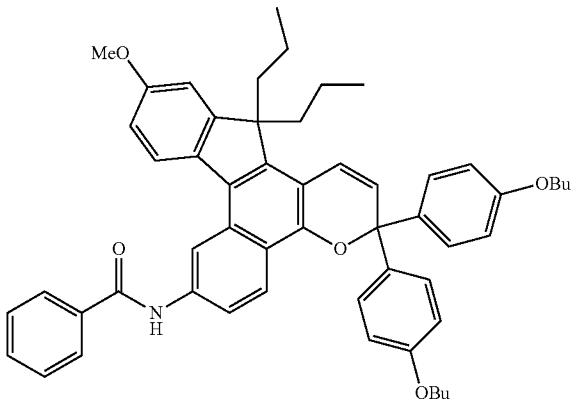 | 83 | 1 |
| Example 13 | 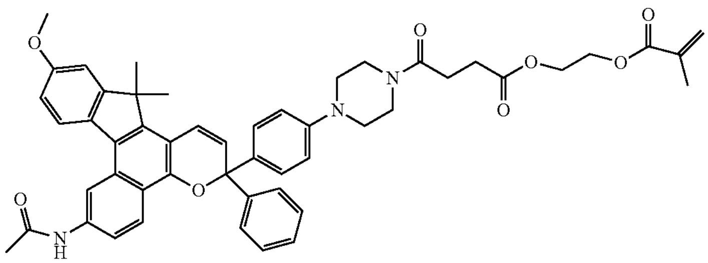 [SMILES: C=C(C)C(=O)OCCOC(=O)CCC(=O)N1CCN(c2ccc(C3(c4ccccc4)C=Cc4c5c(c6cc(NC(C)=O)ccc6c4O3)-c3ccc(OC)cc3C5(C)C)cc2)CC1] | 60 | 1, 2 |
| Example 14 | 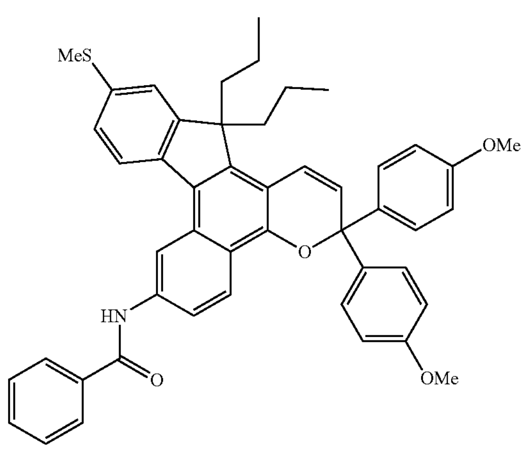 [SMILES: CCCC1(CCC)c2cc(SC)ccc2-c2c1c1c(c3ccc(NC(=O)c4ccccc4)cc23)OC(c2ccc(OC)cc2)(c2ccc(OC)cc2)C=C1] | 56 | 1, 2 |

TABLE 3-continued

Summary of Examples

| Example | Structure | Yield[1] (%) | Characterization 1 = $^1$H NMR 2 = mass spec |
|---|---|---|---|
| Example 15 | 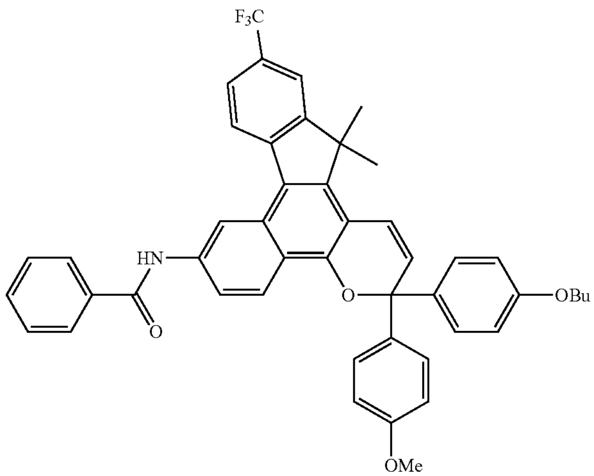 | 78 | 1, 2 |
| Example 16 | 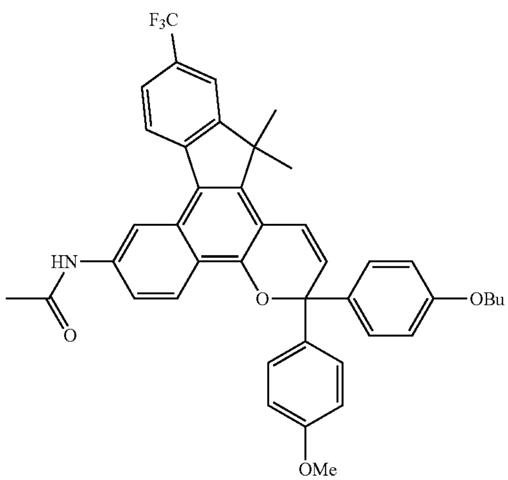 | 72 | 1, 2 |
| Example 17 | 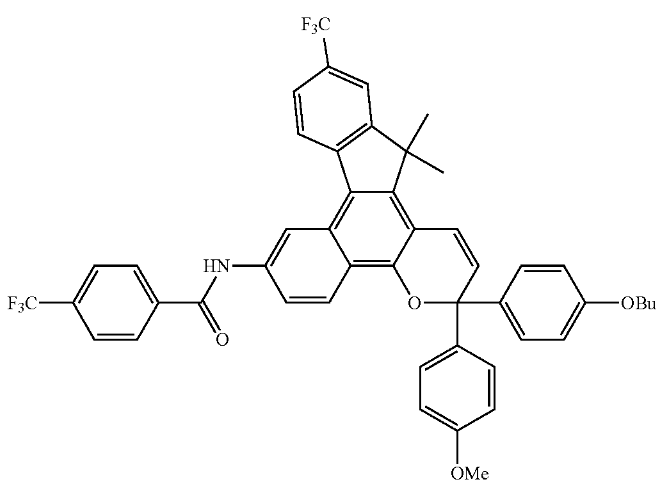 | 75 | 1, 2 |

TABLE 3-continued

Summary of Examples

| Example | Structure | Yield[1] (%) | Characterization 1 = $^1$H NMR 2 = mass spec |
|---|---|---|---|
| Example 18 | (structure with F₃C, MeO-benzamide, OBu, OMe groups) | 70 | 1, 2 |
| Example 19 | (structure with F₃C, dimethylamino-benzamide, OBu, OMe groups) | 65 | 1, 2 |
| Example 20 | (structure with F₃C, 2-methylbenzamide, OBu, OMe groups) | 72 | 1, 2 |

TABLE 3-continued
Summary of Examples
| Example | Structure | Yield[1] (%) | Characterization 1 = $^1$H NMR 2 = mass spec |
|---|---|---|---|
| Example 21 | 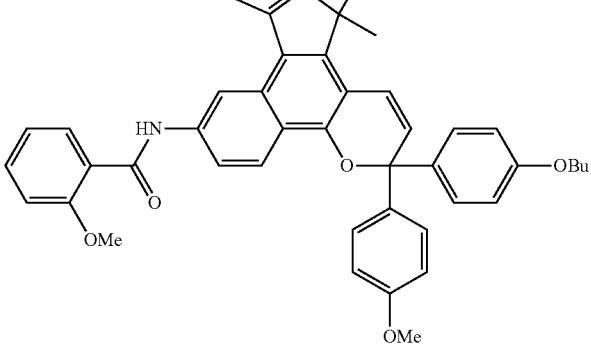 | 68 | 1, 2 |
| Example 22 | 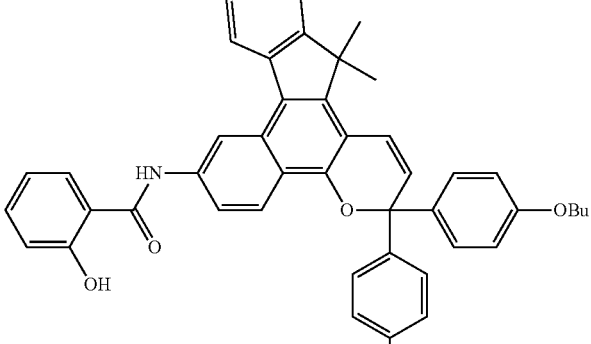 | 62 | 1, 2 |
| Example 23 | 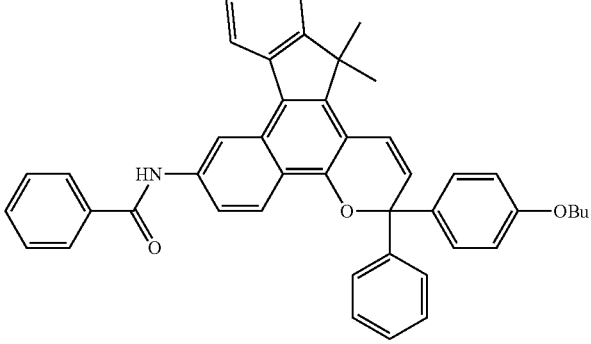 | 75 | 1, 2 |

TABLE 3-continued

Summary of Examples

| Example | Structure | Yield[1] (%) | Characterization 1 = $^1$H NMR 2 = mass spec |
|---|---|---|---|
| Example 24 | 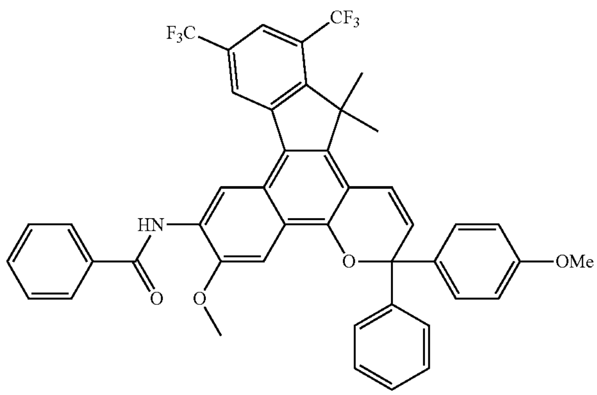 [SMILES: COc1ccc(C2(c3ccccc3)C=Cc3c4c(c5cc(NC(=O)c6ccccc6)c(OC)cc5c3O2)-c2cc(C(F)(F)F)cc(C(F)(F)F)c2C4(C)C)cc1] | 70 | 1, 2 |
| Example 25 | 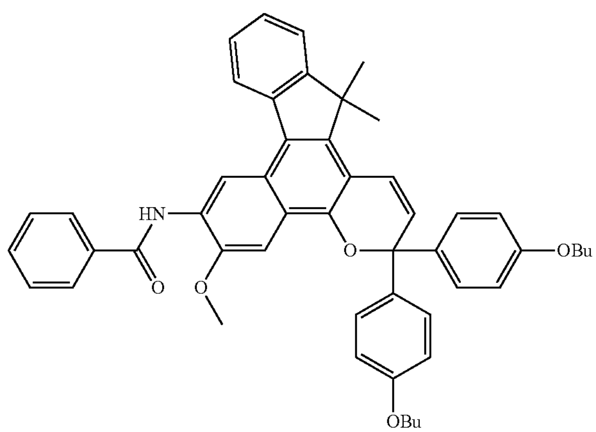 | 65 | 1, 2 |
| Example 26 | 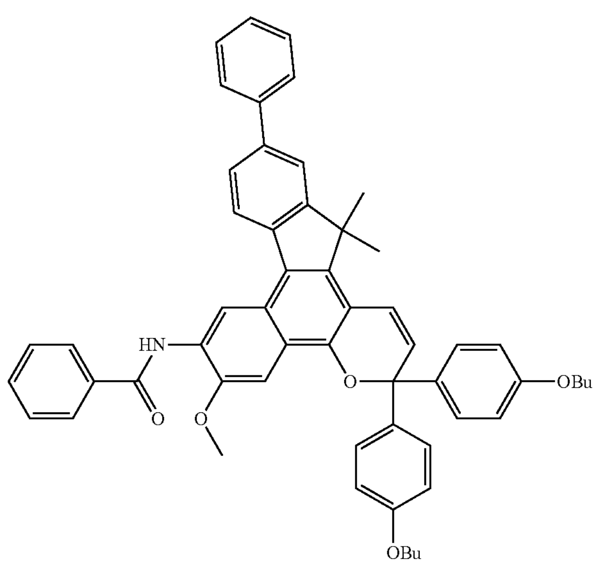 | 72 | 1, 2 |

TABLE 3-continued

Summary of Examples

| Example | Structure | Yield[1] (%) | Characterization 1 = $^1$H NMR 2 = mass spec |
|---|---|---|---|
| Example 27 | 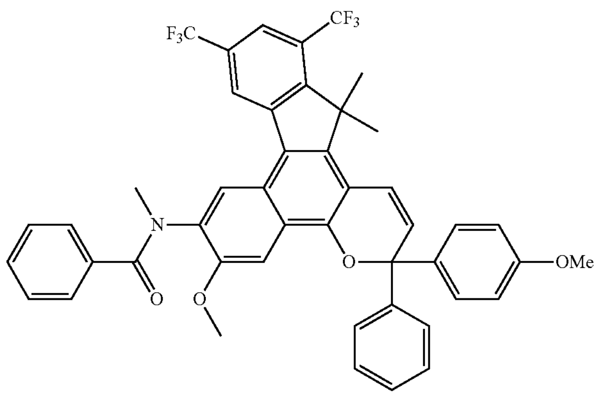 [SMILES: COc1ccc(C2(c3ccccc3)C=Cc3c4c(c5cc(N(C)C(=O)c6ccccc6)c(OC)cc5c3O2)-c2cc(C(F)(F)F)cc(C(F)(F)F)c2C4(C)C)cc1] | 70 | 1, 2 |
| Example 28 | 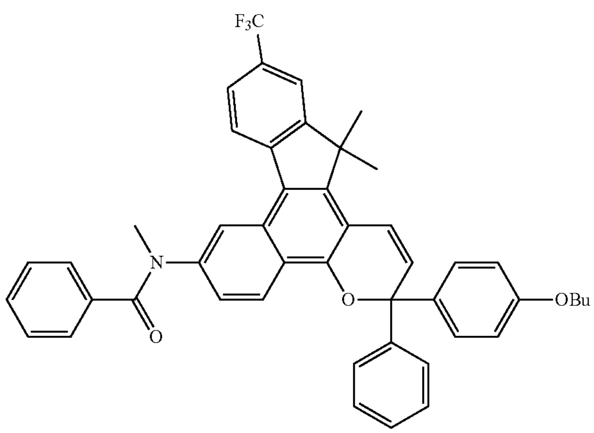 | 72 | 1, 2 |
| Example 29 | 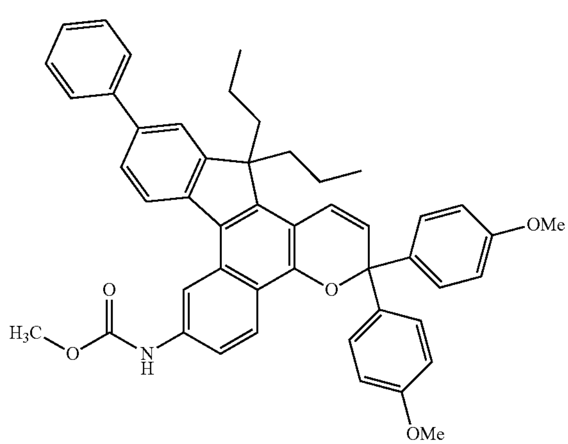 [SMILES: CCCC1(CCC)c2cc(-c3ccccc3)ccc2-c2c1c1c(c3ccc(NC(=O)OC)cc23)OC(c2ccc(OC)cc2)(c2ccc(OC)cc2)C=C1] | | 1, 2 |

TABLE 3-continued

Summary of Examples

| Example | Structure | Yield[1] (%) | Characterization 1 = $^1$H NMR 2 = mass spec |
|---|---|---|---|
| Example 30 | 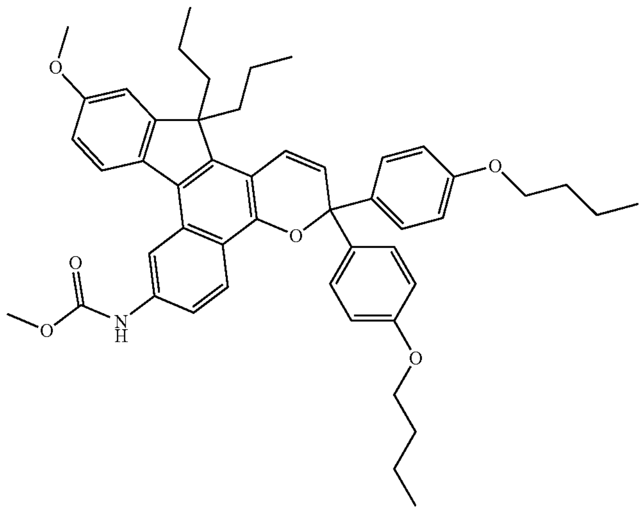 [SMILES: CCCCOc1ccc(C2(c3ccc(OCCCC)cc3)C=Cc3c4c(c5cc(NC(=O)OC)ccc5c3O2)-c2ccc(OC)cc2C4(CCC)CCC)cc1] | | 1, 2 |
| Example 31 | 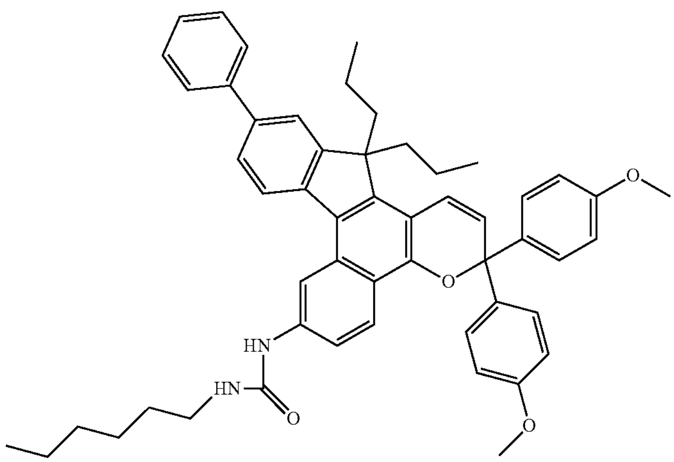 [SMILES: CCCCCCNC(=O)Nc1ccc2c3c(c4c(c2c1)-c1ccc(-c2ccccc2)cc1C4(CCC)CCC)C=CC(c1ccc(OC)cc1)(c1ccc(OC)cc1)O3] | | 2 |

[1]Yield reported corresponds to the step creating the Carbon-Nitrogen bond at the 7-position Part 2: Results Each of the photochromic dyes from Examples 1 through 14 and 24 through 31, and each comparative example shown in Table 4 were incorporated into a polyurethane coating system as described in U.S. Pat. No. 8,608,988 examples 1-3 at the same mol % and applied at the same coating thickness. All samples were cured at 125° C. for 1 hour.

The temperature dependence of the samples was determined by measuring the change in the optical density from the bleached to the darkened state at two temperatures, 10° C. and 35° C. using methods described below. Prior to testing for temperature dependence, each of the coated lenses was conditioned by first being exposed to 365-nanometer ultraviolet light for 10 minutes at a distance of about 14 centimeters to activate the photochromic materials. The UVA (315 to 380 nm) irradiance at the lens was measured with a LICOR® Model Li-1800 spectroradiometer and found to be 22.2 watts per square meter. The lens was then placed under a 500 watt, high intensity halogen lamp for 10 minutes at a distance of about 36 centimeters to bleach (inactivate) the photochromic materials. The illuminance at the lens was measured with the LICOR® spectroradiometer and found to be 21.9 Klux. The lenses, were then kept in a dark environment at room temperature (from 70 to 75° F., or 21 to 24° C.) for at least 1 hour prior to testing on an optical bench. Prior to optical bench measurement, the lenses were measured for ultraviolet absorbance at 390 nanometers. The BMP optical bench was fitted with two 150-watt ORIEL® Model #66057 Xenon arc lamps at right angles to each other. The light path from Lamp 1 was directed through a 3 mm SCLIOTT® KG-2 band-pass filter and appropriate neutral density filters that contributed to the required UV and partial visible light irradiance level. The light path from Lamp 2 was directed through a 3 mm SCLIOTT® KG-2 band-pass filter, a SCLIOTT® short band 400 nm cutoff filter and appropriate neutral density filters in order to provide supplemental visible light illuminance. A 2 inch×2 inch 50% polka dot beam splitter, at 45° to each lamp is used to mix the two beams. The combination of neutral density filters and voltage control of the Xenon arc lamp were used to adjust the intensity of the irradiance. Proprietary software i.e., BMPSoft version 2.1e was used on the BMP to control timing, irradiance, air cell and sample temperature, shuttering, filter selection and response measurement. A ZEISS® spectrophotometer, Model MCS 501, with fiber optic cables for light delivery through the lens was used for response and color measurement. Photopic response measurements were collected on each lens. The power output of the optical bench, i.e., the dosage of light that the lens was exposed to, was adjusted to 6.7 Watts per square meter (W/m$^2$) UVA, integrated from 315-380 nm and 50 Klux illuminance, integrated from 380-780 nm. Measurement of this power setpoint was made using an irradiance probe and the calibrated Zeiss spectrophotometer. The lens sample cell was fitted with a quartz window and self-centering sample holder. The temperature in the sample cell was controlled at 10° C. and 35° C. through the software with a modified Lacis, Model LX-10, environment simulator. Measurement of the sample's dynamic photochromic response and color measurements was made using the same Zeiss spectrophotometer, with fiber optic cables for light delivery from a tungsten halogen lamp and through the sample. The collimated monitoring light beam from the fiber optic cable was maintained perpendicular to the test sample while passing through the sample and directed into a receiving fiber optic cable assembly attached to the spectrophotometer. The exact point of placement of the sample in the sample cell was where the activating xenon arc beam and the monitoring light beam intersected to form two concentric circles of light. The angle of incidence of the xenon arc beam at the sample placement point was =30° from perpendicular. Response measurements, in terms of a change in optical density (ΔOD) from the unactivated or bleached state to the activated or colored state were determined by establishing the initial unactivated transmittance, opening the shutter from the Xenon lamp(s) and measuring the transmittance through activation at selected intervals of time. Change in optical density at a prescribed temperature was determined according to the formula: $\Delta OD_{temp} = \log(10)(\% Tb/\% Ta)$, where % Tb is the percent transmittance in the bleached state, % Ta is the percent transmittance in the activated state both measured at that temperature. Optical density measurements were based on photopic optical density.

The temperature dependence of the samples was determined using the changes in optical density at both 10° C. and 35° C. The measure was calculated as the percent loss of the photopic response between the two temperature, % ΔOD loss=$100*(1-\Delta OD_{35}/\Delta OD_{10})$. The activation time was 15 minutes at 35° C., and 30 minutes at 10° C. Results are reported in Table 4 as % ΔOD loss. The lower the % ΔOD loss, the better the temperature dependence.

Table 4 shows the temperature dependence of selected examples versus comparative examples, grouped according to further substituents. Structures for the examples are found in Table 3.

TABLE 4

| Example/Comparative Example | % ΔOD loss |
|---|---|
| Example 1 | 46.0 |
| Example 2 | 46.1 |
| Example 3 | 43.8 |
| Example 4 | 43.0 |
| Example 5 | 41.7 |
| Example 6 | 46.1 |
| Example 7 | 42.9 |
| Example 8 | 41.5 |
| Example 9 | 42.4 |
| Example 29 | 45 |
| Example 31 | 33 |
| CE-32 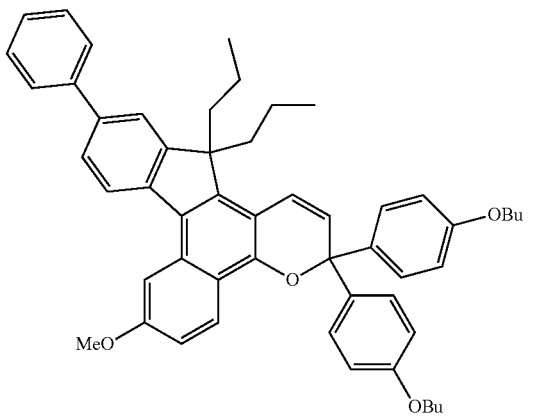 | 53.6 |

TABLE 4-continued
| Example/Comparative Example | | % ΔOD loss |
|---|---|---|
| CE-33 | 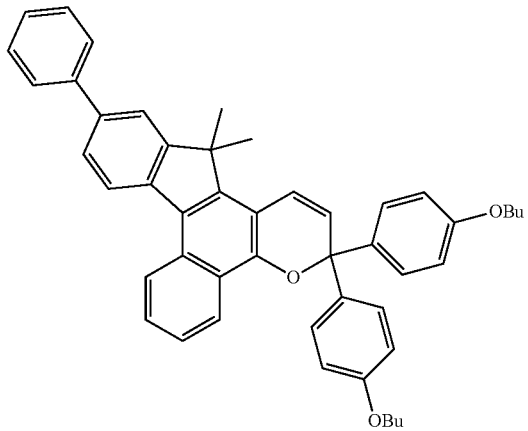 | 55.0 |
| CE-34 | 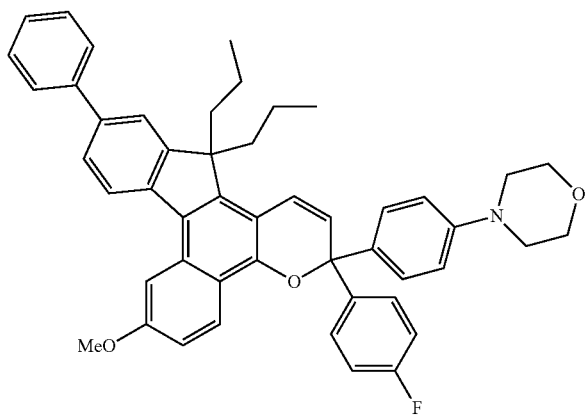 [SMILES: CCCC1(CCC)c2cc(-c3ccccc3)ccc2-c2c1c1c(c3ccc(OC)cc23)OC(c2ccc(F)cc2)(c2ccc(N3CCOCC3)cc2)C=C1] | 55.5 |
| Example 10 | | 47.1 |
| Example 11 | | 45.5 |
| CE-35 | 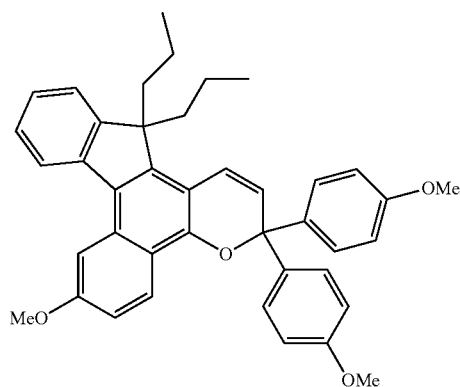 [SMILES: CCCC1(CCC)c2ccccc2-c2c1c1c(c3ccc(OC)cc23)OC(c2ccc(OC)cc2)(c2ccc(OC)cc2)C=C1] | 54.9 |

TABLE 4-continued
| Example/Comparative Example | % ΔOD loss |
|---|---|
| Example 12 | 38.8 |
| Example 30 | 42 |
| CE-36 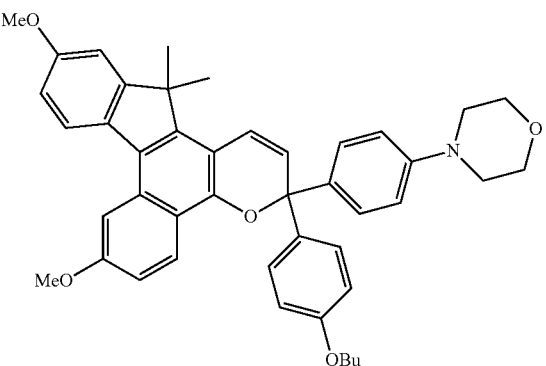 | 50.0 |
| Example 14 | 41.6 |
| CE-37 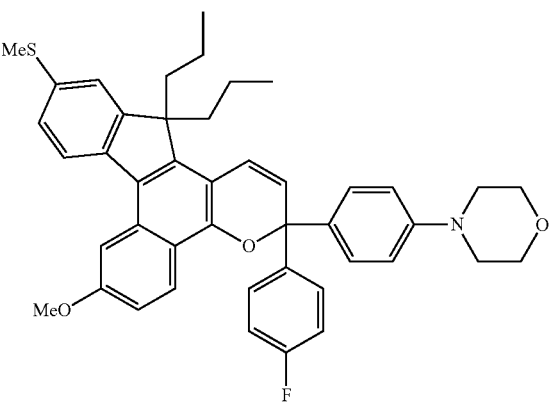 [SMILES: CCCC1(CCC)c2cc(SC)ccc2-c2c1c1c(c3ccc(OC)cc23)OC(c2ccc(F)cc2)(c2ccc(N3CCOCC3)cc2)C=C1] | 51.0 |
| CE-38 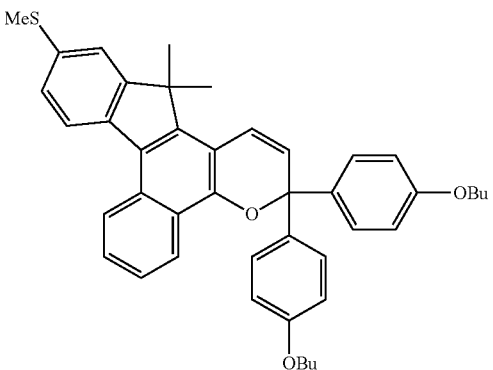 | 55.0 |

TABLE 4-continued

| Example/Comparative Example | | % ΔOD loss |
|---|---|---|
| Example 25 | | 47.3 |
| CE-39 | 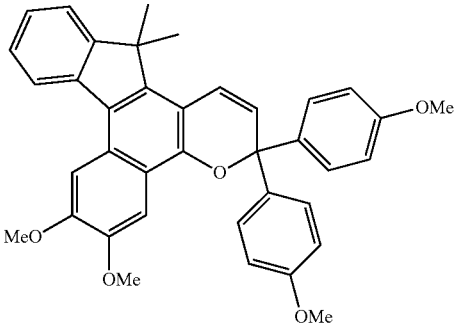 [SMILES: COc1ccc(C2(c3ccc(OC)cc3)C=Cc3c4c(c5cc(OC)c(OC)cc5c3O2)-c2ccccc2C4(C)C)cc1] | 55.3 |
| Example 26 | | 44.6 |
| CE-40 | 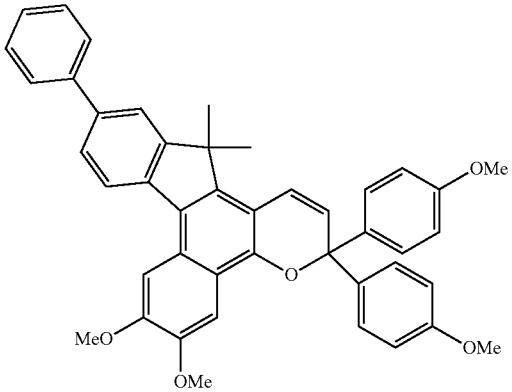 [SMILES: COc1ccc(C2(c3ccc(OC)cc3)C=Cc3c4c(c5cc(OC)c(OC)cc5c3O2)-c2ccc(-c3ccccc3)cc2C4(C)C)cc1] | 53.7 |
| Example 24 | | 63.4 |
| Example 27 | | 60.8 |
| CE-41 | 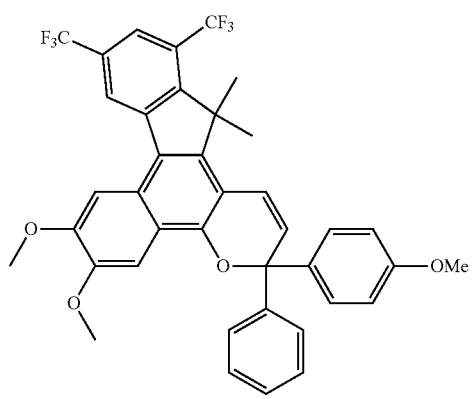 [SMILES: COc1ccc(C2(c3ccccc3)C=Cc3c4c(c5cc(OC)c(OC)cc5c3O2)-c2cc(C(F)(F)F)cc(C(F)(F)F)c2C4(C)C)cc1] | 65.0 |

The results shown in Table 4 clearly demonstrate the improvement in temperature dependence provided by the presence of an amide, carbamate or urea in the 7-position when compared directly with analogous compounds having either a hydrogen or methoxy group in the same positions.

The present invention can further be characterized by one or more of the following non-limiting clauses.

Clause 1. An indenofused naphthopyran having the core skeletal structure represented by Formula (1):

Formula (1)

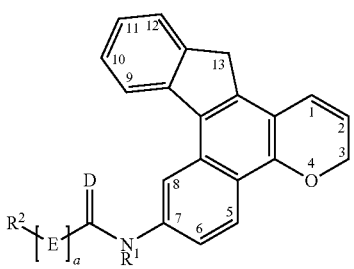

wherein,
D is oxygen or sulfur;
E is oxygen, sulfur, or $NR^{2'}$;
a is 0 or 1;
$R^1$ is hydrogen, or substituted or unsubstituted alkyl;
$R^2$ and $R^{2'}$ are each independently selected from hydrogen, substituted or unsubstituted alkyl, substituted or unsubstituted aryl, substituted or unsubstituted heteroaryl, or substituted or unsubstituted heterocycloalkyl;
provided that when $R^2$ is a substituted aryl or substituted heteroaryl, the substituent does not comprise an aromatic group or a cyclic group; and
provided that when E is oxygen or sulfur, $R^2$ is not hydrogen.

Clause 2. The indenofused naphthopyran of clause 1, wherein,
$R^1$ is hydrogen or alkyl, and
$R^2$ is alkyl, or substituted or unsubstituted aryl.

Clause 3. The indenofused naphthopyran of clauses 1 or 2, having the skeletal structure represented by Formula (Ia):

Formula (Ia)

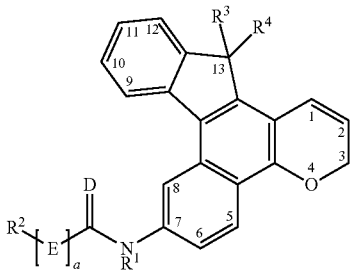

wherein,
$R^3$ and $R^4$ are each independently selected from
(i) hydrogen, substituted or unsubstituted alkyl, substituted or unsubstituted heterocycloalkyl, allyl, substituted or unsubstituted aryl, or substituted or unsubstituted heteroaryl;
(ii) alkoxy, hydroxyl, alkylthio, ketone, aldehyde, ester, carboxylic acid, carboxylate, siloxane, alkoxysilane, or polysiloxane;
(iii) a group comprising polyester, a polyether, polycarbonate, a polyurethane or combinations thereof; or
(iv) $R^3$ and $R^4$ together form a spiro substituent selected from a substituted or unsubstituted spiro-carbocyclic ring containing 3 to 10 carbon atoms, a substituted or unsubstituted spiro-heterocyclic ring containing 1 or 2 oxygen atoms and 3 to carbon atoms including the spirocarbon atom, the spiro-carbocyclic ring and spiro-heterocyclic ring being annellated with 0, 1 or 2 benzene rings, each spiro-ring substituent independently being alkyl.

Clause 4. The indenofused naphthopyran of clause 3, wherein $R^3$ and $R^4$ are each independently selected from substituted or unsubstituted alkyl.

Clause 5. The indeno fused naphthopyran of clauses 3 or 4, having the core skeletal structure represented by Formula (Ib):

Formula (Ib)

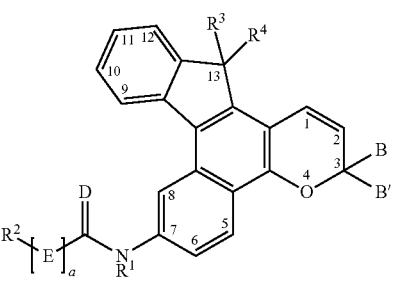

wherein,
B and B' are each independently selected from substituted or unsubstituted aryl, substituted or unsubstituted heteroaryl, substituted or unsubstituted alkenyl, or substituted or unsubstituted alkynyl, or B and B' taken together form a ring structure.

Clause 6. The indenofused naphthopyran of clause 5, wherein B and B' are each independently selected from substituted or unsubstituted aryl.

Clause 7. The indenofused naphthopyran of clause 5, wherein B and B' are each independently selected from substituted or unsubstituted phenyl, alkoxyphenyl, halo phenyl, or morpholino phenyl.

Clause 8. The indenofused naphthopyran of any of clauses 5 to 7, having the core skeletal structure represented by Formula (Ic):

Formula (Ic)

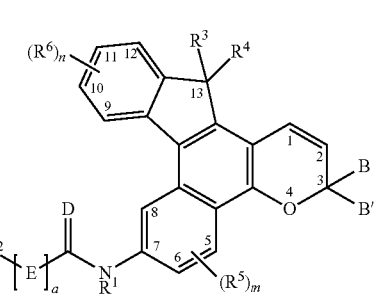

wherein,
m is 0 to 3, and n is 0 to 4; and
$R^5$ independently for each m, and $R^6$ independently for each n, are each independently selected from:
i. hydroxyl;
ii. cyano;
iii. acrylate or methacrylate;
iv. amino or nitrogen-containing heterocycle;
v. a lengthening group $L^1$;
vi. halogen selected from fluoro, chloro, bromo, or iodo;
vii. substituted or unsubstituted alkyl;
viii. haloalkyl;
ix. perhaloalkyl;
x. boronic ester or boronic acid;
xi. polyether, polyester, polycarbonate, or polyurethane;
xii. substituted or unsubstituted aryl;

xiii. substituted or unsubstituted heterocycloalkyl;
xiv. substituted or unsubstituted heteroaryl; or
xv. alkoxy, hydroxyl, alkylthio, ketone, aldehyde, ester, carboxylic acid, carboxylate, amide, urea, siloxane, alkoxysilane, polysiloxane, carbonate, or carbamate.

Clause 9. The indenofused naphthopyran of clause 8, wherein $R^5$ independently for each m and $R^6$ independently for each n, are each independently selected from halogen, alkyoxy, perhaloalkyl, or substituted or unsubstituted aryl.

Clause 10. The indenofused naphthopyran of clause 8, wherein each lengthening group $L^1$ is independently represented by the following Formula (III),

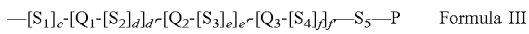

$$—[S_1]_c—[Q_1-[S_2]_d]_{d'}—[Q_2-[S_3]_e]_{e'}—[Q_3-[S_4]_f]_{f'}—S_5—P \quad \text{Formula III}$$

wherein:
(a) $Q_1$, $Q_2$, and $Q_3$ for each occurrence, are independently a divalent group selected from the group consisting of unsubstituted aryl, substituted aryl, unsubstituted heteroaryl, substituted heteroaryl, unsubstituted cycloalkyl, substituted cycloalkyl, unsubstituted heterocycloalky, or substituted heterocycloalkyl;
wherein the aryl substituents, heteroaryl substituents, cycloalkyl substituents, and heterocycloalkyl substituents are each independently selected from the group consisting of P, liquid crystal mesogens, halogen, poly($C_1-C_{18}$ alkoxy), $C_1-C_{18}$ alkoxycarbonyl, $C_1-C_{18}$ alkylcarbonyl, $C_1-C_{18}$ alkoxycarbonyloxy, aryloxycarbonyloxy, perfluoro($C_1-C_{18}$) alkoxy, perfluoro($C_1-C_{18}$)alkoxycarbonyl, perfluoro($C_1-C_{18}$)alkylcarbonyl, perfluoro($C_1-C_{18}$)alkylamino, di-(perfluoro($C_1-C_{18}$)alkyl)amino, perfluoro($C_1-C_{18}$)alkylthio, $C_1-C_{18}$ alkylthio, $C_3-C_{10}$ cycloalkoxy, or $C_1-C_{18}$ alkyl;
(b) c, d, e, and f are each independently chosen from an integer of 1 to 20; and each $S_1$, $S_2$, $S_3$, $S_4$, and $S_5$ is independently chosen for each occurrence from a spacer unit selected from the group consisting of:
(i) alkylene, substituted alkylene, haloalkylene, substituted haloalkylene, —Si($CH_2$)$_g$—, or —(Si[($CH_3$)$_2$]O)$_h$—, wherein g for each occurrence is independently chosen from an integer from 1 to 20; h for each occurrence is independently chosen from an integer from 1 to 16; and the substituents for the alkylene and haloalkylene are independently selected from the group consisting of $C_1-C_{18}$ alkyl and aryl;
(ii) —N(Z)—, —C(Z)=C(Z)—, —C(Z)=N—, —C(Z')$_2$—C(Z')$_2$—, —N(Z)—C(Z)$_2$—, and a single bond, wherein Z for each occurrence is independently selected from the group consisting of hydrogen, $C_1-C_{18}$ alkyl, or aryl, and Z' for each occurrence is independently selected from the group consisting of alkyl or aryl; or
(iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1-C_{24}$ alkylene residue, the $C_1-C_{24}$ alkylene residue being unsubstituted, mono-substituted by cyano or halogen, or poly-substituted by halogen,
provided that when two spacer units comprising heteroatoms are linked together the spacer units are linked so that heteroatoms are not directly linked to each other;
(c) P is hydrogen; and
(d) d', e' and f' are each independently chosen from 0, 1, 2, 3, and 4, provided that the sum of d'+e'+f' is at least 1.

Clause 11. The indenofused naphthopyran of any of clauses 1 to 10, wherein each alkyl substituent, each heterocycloalkyl substituent, each aryl substituent, or each heteroaryl substituent, is in each case independently selected from halogen, cyano, nitro, alkyl, alkenyl, alkynyl, haloalkyl, perhaloalkyl, heterocycloalkyl, aryl, heteroaryl, alkoxy, hydroxyl, alkylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a methacrylate group, or combinations thereof.

Clause 12. The indeno fused naphthopyran of clause 11, wherein each alkyl substituent, each heterocycloalkyl substituent, each aryl substituent, or each heteroaryl substituent can be further substituted with alkyl, haloalkyl, perhaloalkyl, aryl, heteroaryl, phenylalkyl, monoalkyl substituted phenylalkyl, monoalkoxy substituted phenylalkyl, alkoxyalkyl, heterocycloalkyl, polysiloxane, hydroxyl, ether, polyether, polyester, an acrylate group, a methacrylate group, polycarbonate, halogen, or combinations thereof.

Clause 13. A photochromic composition comprising the indeno fused naphthopyran of any of clauses 1 to 12.

Clause 14. A photochromic article comprising the indenofused naphthopyran of any of clauses 1 to 12, wherein the photochromic article is selected from ophthalmic articles, display articles, windows, mirrors, active liquid crystal cell articles, or passive liquid crystal cell articles.

Clause 15. The photochromic article of clause 14, wherein the photochromic article is selected from ophthalmic articles, and the ophthalmic articles are selected from corrective lenses, non-corrective lenses, contact lenses, intraocular lenses, magnifying lenses, protective lenses, or visors.

Clause 16. The photochromic article of clause 15, wherein the photochromic article is selected from display articles, and the display articles are selected from screens, monitors, or security elements.

Clause 17. An indeno-fused naphthopyran, represented by Formula (Ic):

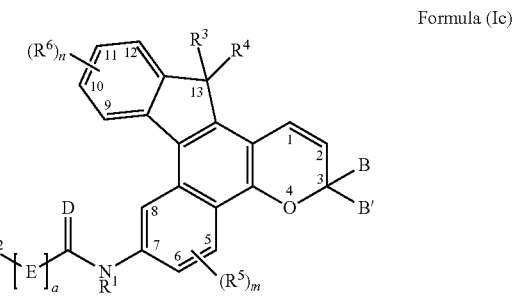

Formula (Ic)

wherein,
D is oxygen or sulfur;
E is oxygen, sulfur, or $NR^{2'}$;
a is 0 or 1;
$R^1$ is hydrogen, or substituted or unsubstituted alkyl;
$R^2$ and $R^{2'}$ are each independently selected from hydrogen, substituted or unsubstituted alkyl, substituted or unsubstituted aryl, substituted or unsubstituted heteroaryl, or substituted or unsubstituted heterocycloalkyl;
provided that when $R^2$ is a substituted aryl or substituted heteroaryl, the substituent does not comprise an aromatic group or a cyclic group;
provided that when E is oxygen or sulfur, $R^2$ is not hydrogen;
m is 0 to 3;
n is 0 to 4; and
$R^3$, $R^4$, $R^5$, $R^6$, B, and B' are independently selected from hydrogen or a group other than hydrogen.

Clause 18. The indeno-fused naphthopyran of clause 17, wherein,
$R^1$ is hydrogen or unsubstituted alkyl, and
$R^2$ is substituted or unsubstituted alkyl, or substituted or unsubstituted aryl.

Clause 19. The indeno-fused naphthopyran of clauses 17 or 18, wherein,
$R^3$ and $R^4$ are each independently selected from
(i) hydrogen, substituted or unsubstituted alkyl, substituted or unsubstituted heterocycloalkyl, allyl, substituted or unsubstituted aryl, or substituted or unsubstituted heteroaryl;
(ii) alkoxy, hydroxyl, alkylthio, ketone, aldehyde, ester, carboxylic acid, carboxylate, siloxane, alkoxysilane, or polysiloxane;
(iii) a group comprising polyester, polyether, polycarbonate, polyurethane or combinations thereof; or
(iv) $R^3$ and $R^4$ together form an aliphatic ring having 3 to 20 ring member carbon atoms, a condensed polycyclic ring having an aromatic ring or aromatic hetero ring condensed to the above aliphatic ring, a hetero ring having 3 to 20 ring member atoms, or a condensed polycyclic ring having an aromatic ring or aromatic hetero ring condensed to the above hetero ring, together with the 13-position carbon atom bonded thereto.

Clause 20. The indeno-fused naphthopyran of any of clauses 17 to 19, wherein $R^3$ and $R^4$, are each independently selected from substituted or unsubstituted alkyl.

Clause 21. The indeno-fused naphthopyran of any of clauses 17 to 20, wherein,
B and B' are each independently selected from substituted or unsubstituted aryl, substituted or unsubstituted heteroaryl, substituted or unsubstituted alkenyl, or substituted or unsubstituted alkynyl, or B and B' taken together form a spiro substituent selected from a substituted or unsubstituted spiro-carbocyclic ring, a substituted or unsubstituted spiro-heterocyclic ring, the spiro-carbocyclic ring or spiro-heterocyclic ring being annellated with 0, 1 or 2 aryl rings, each spiro-ring substituent independently being alkyl.

Clause 22. The indeno-fused naphthopyran of any of clauses 17 to 21, wherein B and B' are each independently selected from substituted or unsubstituted aryl.

Clause 23. The indeno-fused naphthopyran of clauses 21 or 22, wherein each aryl substituent is in each case independently selected from aryl amine, alkyl amine, cyclic aminos, heteroaromatics, or combinations thereof.

Clause 24. The indeno-fused naphthopyran of any of clauses 21 to 23, wherein B and B' are each independently selected from substituted or unsubstituted phenyl, alkoxyphenyl, halo phenyl, or morpholino phenyl.

Clause 25. The indeno-fused naphthopyran of any of clauses 17 to 24, wherein,
m is 0 to 3, and n is 0 to 4;
$R^5$ independently for each m, and $R^6$ independently for each n, are each independently selected from:
i. hydroxyl;
ii. cyano;
iii. (meth)acrylate;
iv. amino or nitrogen-containing heterocycle;
v. a lengthening group $L^1$;
vi. halogen selected from fluoro, chloro, bromo, or iodo;
vii. substituted or unsubstituted alkyl;
viii. substituted or unsubstituted alkenyl;
ix. substituted or unsubstituted alkynyl;
x. haloalkyl;
xi. perhaloalkyl;
xii. boronic ester or boronic acid;
xiii. polyether, polyester, polycarbonate, or polyurethane;
xiv. substituted or unsubstituted aryl;
xv. substituted or unsubstituted heterocycloalkyl;
xvi. substituted or unsubstituted heteroaryl; or
xvii. substituted or unsubstituted alkoxy, substituted or unsubstituted alkylthio, substituted or unsubstituted aryloxy, substituted or unsubstituted arylthio, ketone, aldehyde, ester, carboxylic acid, carboxylate, amide, urea, siloxane, alkoxysilane, polysiloxane, carbonate, or carbamate.

Clause 26. The indeno-fused naphthopyran of clause 25, wherein $R^6$ is at the 10-position and is a lengthening group $L^1$.

Clause 27. The indeno-fused naphthopyran of clauses 25 or 26, wherein $R^5$ independently for each m and $R^6$ independently for each n, are each independently selected from halogen, alkyoxy, perhaloalkyl, or substituted or unsubstituted aryl.

Clause 28. The indeno-fused naphthopyran of any of clauses 25 to 27, wherein each lengthening group $L^1$ is independently represented by the following Formula (2),

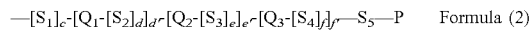

$$—[S_1]_c\text{-}[Q_1\text{-}[S_2]_d]_{d'}\text{-}[Q_2\text{-}[S_3]_e]_{e'}\text{-}[Q_3\text{-}[S_4]_f]_{f'}—S_5—P \quad \text{Formula (2)}$$

wherein:
(a) $Q_1$, $Q_2$, and $Q_3$ for each occurrence, are independently a divalent group selected from the group consisting of unsubstituted aryl, substituted aryl, unsubstituted heteroaryl, substituted heteroaryl, unsubstituted cycloalkyl, substituted cycloalkyl, unsubstituted heterocycloalky, or substituted heterocycloalkyl;

wherein the aryl substituents, heteroaryl substituents, cycloalkyl substituents, and heterocycloalkyl substituents are each independently selected from the group consisting of P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$) alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_3$-$C_{10}$ cycloalkoxy, or $C_1$-$C_{18}$alkyl;

(b) c, d, e, and f are each independently chosen from an integer of 1 to 20; and each $S_1$, $S_2$, $S_3$, $S_4$, and $S_5$ is independently chosen for each occurrence from a spacer unit selected from the group consisting of:
(i) alkylene, substituted alkylene, haloalkylene, substituted haloalkylene, —Si($CH_2$)$_g$—, or —(Si[($CH_3$)$_2$]O)$_h$—, wherein g for each occurrence is independently chosen from an integer from 1 to 20; h for each occurrence is independently chosen from an integer from 1 to 16; and the substituents for the alkylene and haloalkylene are independently selected from the group consisting of $C_1$-$C_{18}$ alkyl or aryl;
(ii) —N(Z)—, —C(Z)=C(Z)—, —C(Z)=N—, —C(Z')$_2$—C(Z')$_2$—, —N(Z)—C(Z)$_2$—, and a single bond, wherein Z for each occurrence is independently selected from the group consisting of hydrogen, $C_1$-$C_{18}$ alkyl or aryl, and Z' for each occurrence is independently selected from the group consisting of $C_1$-$C_{18}$ alkyl or aryl; and
(iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1$-$C_{24}$ alkylene residue, the $C_1$-$C_{24}$ alkylene residue being unsubstituted, mono-substituted by cyano or halogen, or poly-substituted by halogen, provided that when two spacer units comprising heteroatoms are linked together the spacer units are linked so that heteroatoms are not directly linked to each other;
(c) P is hydrogen; and
(d) d', e' and f' are each independently chosen from 0, 1, 2, 3, and 4, provided that the sum of d'+e'+f' is at least 1.

Clause 29. The indeno-fused naphthopyran of any of clauses 17 to 28, wherein each alkyl substituent, each aryl substituent, each heterocycloalkyl substituent, and each heteroaryl substituent, is in each case independently selected from halogen, cyano, nitro, alkyl, alkenyl, alkynyl, haloalkyl, perhaloalkyl, heterocycloalkyl, aryl, heteroaryl, alkoxy, hydroxyl, alkylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a methacrylate group, or combinations thereof.

Clause 30. The indeno-fused naphthopyran of clause 29, wherein each alkyl substituent, each aryl substituent, each heterocycloalkyl substituent, or each heteroaryl substituent, is in each case independently further substituted with an acrylate group or a methacrylate group.

Clause 31. The indeno-fused naphthopyran of any of clauses 1 to 30, wherein the formula comprises at least one additional substituent, identical or different, located on at least one available position on the core skeletal structure among positions 1 to 13 depicted therein.

Clause 32. The indeno-fused naphthopyran of clause 31, wherein said at least one additional substituent is independently selected from alkyl group, heterocycloalkyl group, aryl group, heteroaryl group, thiol groups, alkylthio groups, ketone groups, aldehyde groups, ester groups, carboxylic acid groups, phosphoric acid groups, phosphoric acid ester groups, sulfonic acid groups, sulfonic acid ester groups, nitro groups, cyano groups, alkyl groups, aralkyl groups, alkenyl groups, alkynyl groups, haloalkyl groups, perhaloalkyl groups, heterocycloalkyl groups, aryl groups, alkaryl groups, hydroxyl substituted aryl groups, alkoxy substituted aryl groups, heterocycloalkyl substituted aryl groups, halo substituted aryl groups, poly-fused-ring aryl groups, heteroaryl groups, poly-fused-ring heteroaryl groups, amine groups, carboxylate groups, siloxane groups, alkoxysilane groups, polysiloxane groups, amide groups, carbamate groups, carbonate groups, urea groups, polyester groups, polyether groups, polycarbonate groups, polyurethane groups, acrylate groups, methacrylate groups, aryl amino groups, cyclic amino groups, heteroaromatic groups, or combinations thereof.

Clause 33. A photochromic composition comprising the indeno-fused naphthopyran of any of clauses 17 to 32.

Clause 34. A photochromic article comprising the indeno-fused naphthopyran of any of clauses 17 to 32, wherein the photochromic article is selected from ophthalmic articles, display articles, windows, mirrors, active liquid crystal cell articles, or passive liquid crystal cell articles.

Clause 35. The photochromic article of clause 34, wherein the photochromic article is selected from ophthalmic articles, and the ophthalmic articles are selected from corrective lenses, non-corrective lenses, contact lenses, intraocular lenses, magnifying lenses, protective lenses, or visors.

Clause 36. The photochromic article of clause 35 wherein the photochromic article is selected from display articles, and the display articles are selected from screens, monitors, or security elements.

The present invention has been described with reference to specific details of particular embodiments thereof. It is not intended that such details be regarded as limitations upon the scope of the invention except insofar as to the extent that they are included in the accompanying claims.

What is claimed is:
1. An indeno-fused naphthopyran comprising a core skeletal structure represented by Formula (I):

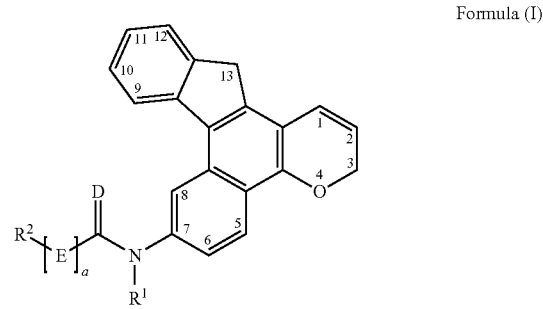

Formula (I)

wherein,
D is oxygen or sulfur;
E is oxygen, sulfur, or $NR^{2'}$;
a is 0 or 1;
$R^1$ is hydrogen, or substituted or unsubstituted alkyl;
$R^2$ and $R^{2'}$ are each independently selected from the group consisting of hydrogen, substituted or unsubstituted alkyl, substituted or unsubstituted aryl, substituted or unsubstituted heteroaryl, and substituted or unsubstituted heterocycloalkyl;
provided that when $R^2$ is a substituted aryl or substituted heteroaryl, the substituent does not comprise an aromatic group or a cyclic group; and
provided that when E is oxygen or sulfur, $R^2$ is not hydrogen.

2. The indeno-fused naphthopyran of claim 1, wherein,
$R^1$ is hydrogen or unsubstituted alkyl, and
$R^2$ is substituted or unsubstituted alkyl, or substituted or unsubstituted aryl.

3. The indeno-fused naphthopyran of claim 1, having the core skeletal structure represented by Formula (Ia):

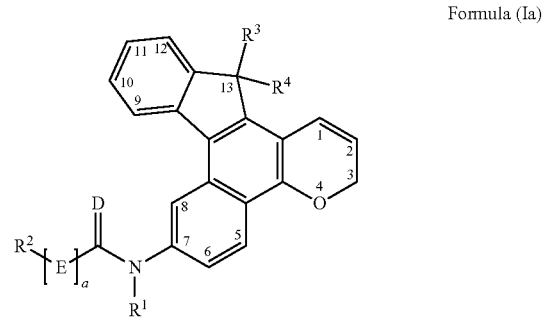

Formula (Ia)

wherein, $R^3$ and $R^4$ are each independently selected from the group consisting of
(i) hydrogen, substituted or unsubstituted alkyl, substituted or unsubstituted heterocycloalkyl, allyl, substituted or unsubstituted aryl, or substituted or unsubstituted heteroaryl;

(ii) alkoxy, hydroxyl, alkylthio, ketone, aldehyde, ester, carboxylic acid, carboxylate, siloxane, alkoxysilane, or polysiloxane;

(iii) a group comprising polyester, polyether, polycarbonate, polyurethane or combinations thereof; and (iv) $R^3$ and $R^4$ together form an aliphatic ring having 3 to 20 ring member carbon atoms, a condensed polycyclic ring having an aromatic ring or aromatic hetero ring condensed to the above aliphatic ring, a hetero ring having 3 to 20 ring member atoms, or a condensed polycyclic ring having an aromatic ring or aromatic hetero ring condensed to the above hetero ring, together with the 13-position carbon atom bonded thereto.

4. The indeno-fused naphthopyran of claim 3, wherein $R^3$ and $R^4$, are each independently substituted or unsubstituted alkyl.

5. The indeno-fused naphthopyran of claim 3, comprising the core skeletal structure represented by Formula (Ib):

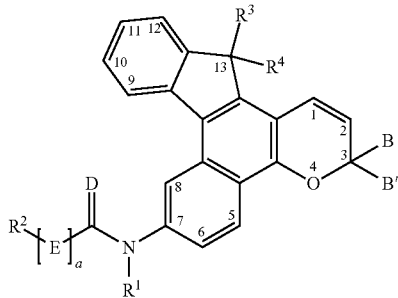

Formula (Ib)

wherein,

B and B' are each independently selected from the group consisting of substituted or unsubstituted aryl, substituted or unsubstituted heteroaryl, substituted or unsubstituted alkenyl, and substituted or unsubstituted alkynyl, or B and B' taken together form an aliphatic ring having 3 to 20 ring member carbon atoms, a condensed polycyclic ring having an aromatic ring or aromatic hetero ring condensed to the above aliphatic ring, a hetero ring having 3 to 20 ring member atoms, or a condensed polycyclic ring having an aromatic ring or aromatic hetero ring condensed to the above hetero ring, together with the 3-position carbon atom bonded thereto.

6. The indeno-fused naphthopyran of claim 5, wherein B and B' are each independently substituted or unsubstituted aryl.

7. The indeno-fused naphthopyran of claim 5, wherein B and B' are each independently selected from the group consisting of substituted or unsubstituted phenyl, alkoxyphenyl, halo phenyl, and morpholino phenyl.

8. The indeno-fused naphthopyran of claim 5, comprising the core skeletal structure represented by Formula (Ic):

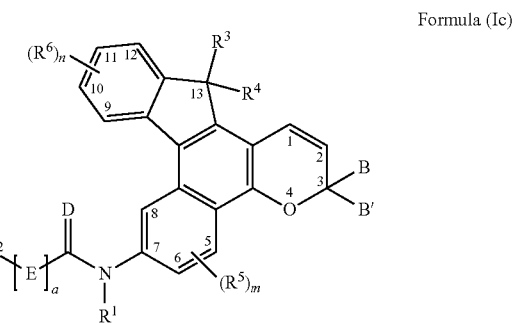

Formula (Ic)

wherein, m is 0 to 3, and n is 0 to 4; and $R^5$ independently for each m, and $R^6$ independently for each n, are each independently:
i. hydroxyl;
ii. cyano;
iii. (meth)acrylate;
iv. amino or nitrogen-containing heterocycle;
v. a lengthening group $L^1$;
vi. halogen selected from fluoro, chloro, bromo, or iodo;
vii. substituted or unsubstituted alkyl;
viii. substituted or unsubstituted alkenyl;
ix. substituted or unsubstituted alkynyl;
x. haloalkyl;
xi. perhaloalkyl;
xii. boronic ester or boronic acid;
xiii. polyether, polyester, polycarbonate, or polyurethane;
xiv. substituted or unsubstituted aryl;
xv. substituted or unsubstituted heterocycloalkyl;
xvi. substituted or unsubstituted heteroaryl; or
substituted or unsubstituted alkoxy, substituted or unsubstituted alkylthio, substituted or unsubstituted aryloxy, substituted or unsubstituted arylthio, ketone, aldehyde, ester, carboxylic acid, carboxylate, amide, urea, siloxane, alkoxysilane, polysiloxane, carbonate, or carbamate.

9. The indeno-fused naphthopyran of claim 8, wherein $R^6$ is at the 10-position and $R^6$ is the lengthening group $L^1$.

10. The indeno-fused naphthopyran of claim 8, wherein $R^5$ independently for each m and $R^6$ independently for each n, are each independently selected from the group consisting of halogen, alkyoxy, perhaloalkyl, and substituted or unsubstituted aryl.

11. The indeno-fused naphthopyran of claim 8, wherein the lengthening group $L^1$ is independently in each instance represented by the following Formula (2), $$-[S_1]_c-[Q_1-[S_2]_d]_{d'}-[Q_2-[S_3]_e]_{e'}-[Q_3-[S_4]_f]_{f'}-S_5-P \quad \text{Formula (2)}$$

wherein:

(a) $Q_1$, $Q_2$, and $Q_3$ for each occurrence, are independently a divalent group selected from the group consisting of unsubstituted aryl, substituted aryl, unsubstituted heteroaryl, substituted heteroaryl, unsubstituted cycloalkyl, substituted cycloalkyl, unsubstituted heterocycloalky, and substituted heterocycloalkyl;

wherein the aryl substituents, heteroaryl substituents, cycloalkyl substituents, and heterocycloalkyl substituents are each independently selected from the group consisting of P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_3$-$C_{10}$ cycloalkoxy, and alkyl;

(b) c, d, e, and f are each independently an integer of 1 to 20; and each $S_1$, $S_2$, $S_3$, $S_4$, is independently for each occurrence a spacer unit selected from the group consisting of:

(i) alkylene, substituted alkylene, haloalkylene, substituted haloalkylene, —Si($CH_2$)$_g$—, or —(Si[$CH_3$]$_2$O)$_h$—, wherein g for each occurrence is independently an integer from 1 to 20; h for each occurrence is independently an integer from 1 to 16; and the substituents for the alkylene and haloalkylene are independently selected from the group consisting of alkyl and aryl;

(ii) —N(Z)—, —C(Z)=C(Z)—, —C(Z)=N—, —C(Z')$_2$—C(Z')$_2$—, —N(Z)—C(Z)$_2$-, and a single bond, wherein Z for each occurrence is independently selected from the group consisting of hydrogen, alkyl, or aryl, and Z' for each occurrence is independently selected from the group consisting of alkyl and aryl; and (iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1$-$C_{24}$ alkylene residue, the $C_1$-$C_{24}$ alkylene residue being unsubstituted, mono-substituted by cyano or halogen, or poly-substituted by halogen, provided that when two spacer units comprising heteroatoms are linked together the spacer units are linked so that heteroatoms are not directly linked to each other;

(c) P is hydrogen; and (d) d', e' and f' are each independently 0, 1, 2, 3, and 4, provided that the sum of d'+e'+f' is at least 1.

12. The indeno-fused naphthopyran of claim 1, wherein each alkyl substituent, each aryl substituent, each heterocycloalkyl substituent, and each heteroaryl substituent, is in each case independently halogen, cyano, nitro, alkyl, alkenyl, alkynyl, haloalkyl, perhaloalkyl, heterocycloalkyl, aryl, heteroaryl, alkoxy, hydroxyl, alkylthio, ketone, aldehyde, ester, carboxylic acid, carboxylate, siloxane, alkoxysilane, polysiloxane, amide, amine, carbamate, carbonate, urea, polyester group, polyether group, polycarbonate group, polyurethane group, an acrylate group, a methacrylate group, aryl amine, alkyl amine, cyclic aminos, heteroaromatics, or combinations thereof.

13. The indeno-fused naphthopyran of claim 12, wherein each of the alkyl substituents, each of the aryl substituents, each of the heterocycloalkyl substituents, and each of the heteroaryl substituents, is in each case independently further substituted with an acrylate group or a methacrylate group.

14. A photochromic composition comprising the indeno-fused naphthopyran of claim 1.

15. A photochromic article comprising the indeno-fused naphthopyran of claim 1,
wherein the photochromic article is selected from the group consisting of ophthalmic articles, display articles, windows, mirrors, active liquid crystal cell articles, and passive liquid crystal cell articles; or
wherein the photochromic article is an ophthalmic article, and the ophthalmic articles is selected from the group consisting of corrective lenses, non-corrective lenses, contact lenses, intra-ocular lenses, magnifying lenses, protective lenses, and visors; or
wherein the photochromic article is a display article, and the display articles is selected from the group consisting of screens, monitors, and security elements.

* * * * *

UNITED STATES PATENT AND TRADEMARK OFFICE
CERTIFICATE OF CORRECTION

PATENT NO. : 11,518,751 B2
APPLICATION NO. : 17/058888
DATED : December 6, 2022
INVENTOR(S) : Robert W. Walters et al.

It is certified that error appears in the above-identified patent and that said Letters Patent is hereby corrected as shown below:

On the Title Page

Column 1, Line 9, delete "PC/EP2018/06.389.3" and insert -- PCT/EP2018/063893 --

In the Specification

Column 59, Line 9, delete "alkyoxy" and insert -- alkoxy --

Column 62, Line 19, delete "alkyoxy" and insert -- alkoxy --

In the Claims

Column 66, Line 46, Claim 9, delete "10-position" and insert -- 10-position, --

Column 66, Line 50, Claim 10, delete "alkyoxy" and insert -- alkoxy --

Column 66, Lines 63-64, Claim 11, delete "heterocycloalky," and insert -- heterocycloalkyl, --

Column 67, Line 10, Claim 11, after "$S_4$," insert -- and $S_5$ --

Column 67, Lines 14-15, Claim 11, delete "--(Si[CH$_3$)$_2$]O)$_h$--," and insert -- --(Si[(CH$_3$)$_2$]O)$_h$--, --

Column 67, Line 23, Claim 11, delete "C(Z)$_2$-," and insert -- C(Z)$_2$--, --

Signed and Sealed this
Twenty-sixth Day of September, 2023

Katherine Kelly Vidal
*Director of the United States Patent and Trademark Office*